(12) United States Patent
Allen et al.

(10) Patent No.: US 12,341,463 B2
(45) Date of Patent: Jun. 24, 2025

(54) BLOOD PUMP CONTROLLER AND SYSTEM

(71) Applicant: STAR BP, INC., Spring, TX (US)

(72) Inventors: Jared D. Allen, Apex, NC (US); Sean K. Barry, Yukon, OK (US); Dana G. Pelletier, Newcastle, OK (US); J. Ryan Stanfield, Sandy, UT (US)

(73) Assignee: STAR BP, INC., Spring, TX (US)

( * ) Notice: Subject to any disclaimer, the term of this patent is extended or adjusted under 35 U.S.C. 154(b) by 381 days.

(21) Appl. No.: 17/833,256

(22) Filed: Jun. 6, 2022

(65) Prior Publication Data

US 2023/0390548 A1  Dec. 7, 2023

(51) Int. Cl.
| | | |
|---|---|---|
| H02P 7/29 | (2016.01) | |
| A61M 60/178 | (2021.01) | |
| A61M 60/216 | (2021.01) | |
| A61M 60/419 | (2021.01) | |
| A61M 60/585 | (2021.01) | |
| F04D 13/06 | (2006.01) | |
| F04D 15/00 | (2006.01) | |
| G08B 7/06 | (2006.01) | |
| G08B 21/18 | (2006.01) | |
| H02J 7/02 | (2016.01) | |
| H02P 23/00 | (2016.01) | |
| H02P 25/03 | (2016.01) | |

(52) U.S. Cl.
CPC .............. *H02P 7/29* (2013.01); *A61M 60/178* (2021.01); *A61M 60/216* (2021.01); *A61M 60/419* (2021.01); *A61M 60/585* (2021.01); *G08B 7/06* (2013.01); *G08B 21/18* (2013.01); *H02J 7/02* (2013.01); *H02P 23/0004* (2013.01); *H02P 25/03* (2016.02); *F04D 13/06* (2013.01); *F04D 15/0066* (2013.01)

(58) Field of Classification Search
CPC .............. A61M 60/122; A61M 60/216; A61M 60/419; A61M 60/508; A61M 60/538; A61M 60/585; A61M 60/592; A61M 60/871

See application file for complete search history.

(56) References Cited

U.S. PATENT DOCUMENTS

| | | |
|---|---|---|
| 6,949,066 B2 | 9/2005 | Bearnson et al. |
| 7,645,225 B2 | 1/2010 | Medvedev et al. |
| 8,096,935 B2 | 1/2012 | Sutton et al. |

(Continued)

*Primary Examiner* — Said Bouziane
(74) *Attorney, Agent, or Firm* — Ewing & Jones, PLLC

(57) ABSTRACT

A blood pump system includes a blood pump and a corresponding controller. The blood pump includes an impeller that is sealed within the pump housing and hydrodynamically suspended within the pump housing. The pump impeller includes magnets, and is the rotor of a brushless direct current (DC) motor that is driven by electrical signals through stator wire coils in the pump housing, which creates a rotating magnetic field. The rotating magnetic field attracts the magnetized impeller and spins it with the rotating field. The controller provides field-oriented control for the brushless DC motor in the blood pump. The field-oriented control in the controller is provided in a programmable logic device separate from a control processor so that a software or hardware failure related to the control processor does not stop the blood pump. The field-oriented control allows sensing blood flow through the pump without having sensors in the blood stream.

14 Claims, 17 Drawing Sheets

(56) References Cited

U.S. PATENT DOCUMENTS

| | | | |
|---|---|---|---|
| 8,506,470 B2 | 8/2013 | LaRose et al. | |
| 8,562,508 B2 | 10/2013 | Dague et al. | |
| 8,597,350 B2 | 12/2013 | Rudser et al. | |
| 8,721,719 B2 | 5/2014 | Burke | |
| 8,870,552 B2 | 10/2014 | Ayre et al. | |
| 8,905,910 B2 | 12/2014 | Reichenbach et al. | |
| 9,364,596 B2 | 6/2016 | Vadala, Jr. et al. | |
| 9,446,180 B2 | 9/2016 | Vadala, Jr. et al. | |
| 9,526,819 B2 | 12/2016 | Chen | |
| 9,623,161 B2 | 4/2017 | Medvedev et al. | |
| 9,656,010 B2 | 5/2017 | Burke | |
| 9,694,123 B2 | 7/2017 | Bourque et al. | |
| 9,919,088 B2 | 3/2018 | Bonde et al. | |
| 10,471,193 B2 | 11/2019 | Crosby et al. | |
| 10,480,690 B2 | 11/2019 | Kotcharov | |
| 10,507,272 B2 | 12/2019 | Lee et al. | |
| 10,589,011 B2 | 3/2020 | Casas et al. | |
| 10,741,968 B2 | 8/2020 | Stanfield et al. | |
| 10,833,451 B2 | 11/2020 | Stanfield et al. | |
| 10,855,026 B2 | 12/2020 | Stanfield et al. | |
| 10,886,663 B2 | 1/2021 | Stanfield et al. | |
| 10,918,774 B2 | 2/2021 | Stanfield et al. | |
| 11,309,662 B2 | 4/2022 | Stanfield et al. | |
| 11,724,093 B2 | 8/2023 | Stanfield et al. | |
| 2018/0085507 A1* | 3/2018 | Casas | A61M 60/148 |
| 2018/0126053 A1* | 5/2018 | Zilbershlag | A61M 60/216 |
| 2020/0282120 A1* | 9/2020 | Ito | A61M 60/178 |

* cited by examiner

| Alerts | | | |
|---|---|---|---|
| Alert Condition | Detected By | Notification | |
| Pump Low Flow | CP | Pump Low Flow | 1210 |
| Pump Power Over Current | CP | Pump Power High | 1212 |
| Pump Power High | CP | Pump Power High | 1214 |
| Pump Power Low | CP | Pump Power Low | 1216 |
| Pump Speed Low | CP | Pump Speed Low | 1218 |
| Pump Speed Error | CP | Pump Speed Error | 1220 |
| System Over Temp | CP | System Fault | 1222 |
| Reserve Battery Fault | CP | System Fault | 1224 |
| Reserve Battery Low | CP | Reserve Low | 1226 |
| Reserve Battery Discharging | CP | On Reserve | 1228 |
| Primary Battery Low | CP | Battery Low | 1230 |
| Primary Battery Very Low | CP | Battery Very Low | 1232 |
| Primary Battery Critical | CP | Battery Critical | 1234 |
| Control Processor or FPGA Bad | SP | System Fault | 1236 |
| DC Input Bad | CP | System Fault | 1238 |
| Software Failure | SP | System Fault | 1240 |
| Mute Button Stuck | CP | System Fault | 1242 |
| Next Button Stuck | CP | System Fault | 1246 |
| Alert Test | CP | Alert Test | 1248 |

FIG. 12

| Alarms | | |
|---|---|---|
| Alarm Condition | Detected By | Notification |
| Pump Stopped | CP, SP | Pump Stopped |
| Pump Disconnect | CP | Pump Disconnect |
| Pump Re-Start Fail | CP | Pump Re-Start Fail |
| No Primary Battery | CP | No Battery |
| Emergency Alarm Test | CP | Alarm Test |
| Alarm Test | CP | Alarm Test |
| Power Supply Fail | SP | Emergency Alarm |

1400
1410
1412
1414
1416
1418
1420
1422

BLOOD PUMP CONTROLLER AND SYSTEM

BACKGROUND

1. Technical Field

This disclosure generally relates to blood pumps and, more specifically, to blood pump controllers and systems.

2. Background Art

Medical blood pumps augment blood flow for patients with hearts that provide insufficient blood flow. A Ventricular Assist Device (VAD) is one specific type of implantable blood pump. A VAD is placed parallel with a patient's left or right heart ventricle that does not provide the needed blood flow. Known blood pumps use several different pump types and motor configurations and methods for driving these pump motors. Some blood pumps use pump motors to drive radial flow pumps, and others have the motor shaft directly in line with the impeller to drive an axial flow pump to pump the blood. Keeping a reliable seal around the motor shaft into the pump can be problematic. Other pumps use an impeller that is entirely sealed within the pump housing and hydrodynamically suspended within the pump housing. The impeller itself becomes the magnetized rotor part of the motor. The motor stator coils that receive the electrical signals creating the rotating magnetic field to spin the rotor are built right into the pump housing. The entire stator becomes part of the pump flow body itself. Some blood pumps include sensors in the bloodstream to sense pressure and flow. Other blood pumps use various methods to estimate the pressure and or discharge flow of the pump to avoid putting sensors in the bloodstream due to the possibility of blood clots forming around the sensors.

Known apparatus and methods for blood pumps and controllers do not provide precise speed control of the pump or do not allow for direct blood flow sensing without sensors in the bloodstream, and have other disadvantages, e.g., some mechanical pump designs more significantly damage the blood flowing through the pump. Many controllers estimate specific parameters such as pressure or flow rate. These estimates are a source of potential errors in providing proper therapy for a patient, i.e., properly controlling the blood pump. Some failures within a pump controller can stop the blood pump, potentially putting a patient's life in jeopardy. An improved blood pump controller is needed to address these shortcomings in the prior art.

BRIEF SUMMARY

A blood pump system includes a blood pump and a corresponding controller. The blood pump includes an impeller that is sealed within the pump housing and hydrodynamically suspended within the pump housing. The pump impeller includes magnets, and is the rotor of a brushless direct current (DC) motor that is driven by electrical signals through stator wire coils in the pump housing, which creates a rotating magnetic field. The rotating magnetic field attracts the magnetized impeller and spins it with the rotating field. The controller provides field-oriented control for the brushless DC motor in the blood pump. The field-oriented control in the controller is provided in a programmable logic device separate from a control processor so that a software or hardware failure related to the control processor does not stop the blood pump. The field-oriented control allows sensing blood flow through the pump without having sensors in the blood stream.

The foregoing and other features and advantages will be apparent from the following more particular description, as illustrated in the accompanying drawings.

BRIEF DESCRIPTION OF THE SEVERAL VIEWS OF THE DRAWING(S)

The disclosure will be described in conjunction with the appended drawings, where like designations denote like elements, and:

FIG. 12 is a table showing alert conditions and corresponding notifications;

DETAILED DESCRIPTION

A blood pump system includes a blood pump and a corresponding controller. The blood pump includes an impeller that is sealed within the pump housing and hydrodynamically suspended within the pump housing. The pump impeller includes magnets, and is the rotor of a brushless direct current (DC) motor that is driven by electrical signals through stator wire coils in the pump housing, which creates a rotating magnetic field. The rotating magnetic field attracts the magnetized impeller and spins it with the rotating field. The controller provides field-oriented control for the brushless DC motor in the blood pump. The field-oriented control in the controller is provided in a programmable logic device separate from a control processor so that a software or hardware failure related to the control processor does not stop the blood pump. The field-oriented control allows sensing blood flow through the pump without having sensors in the blood stream.

Figure 1:
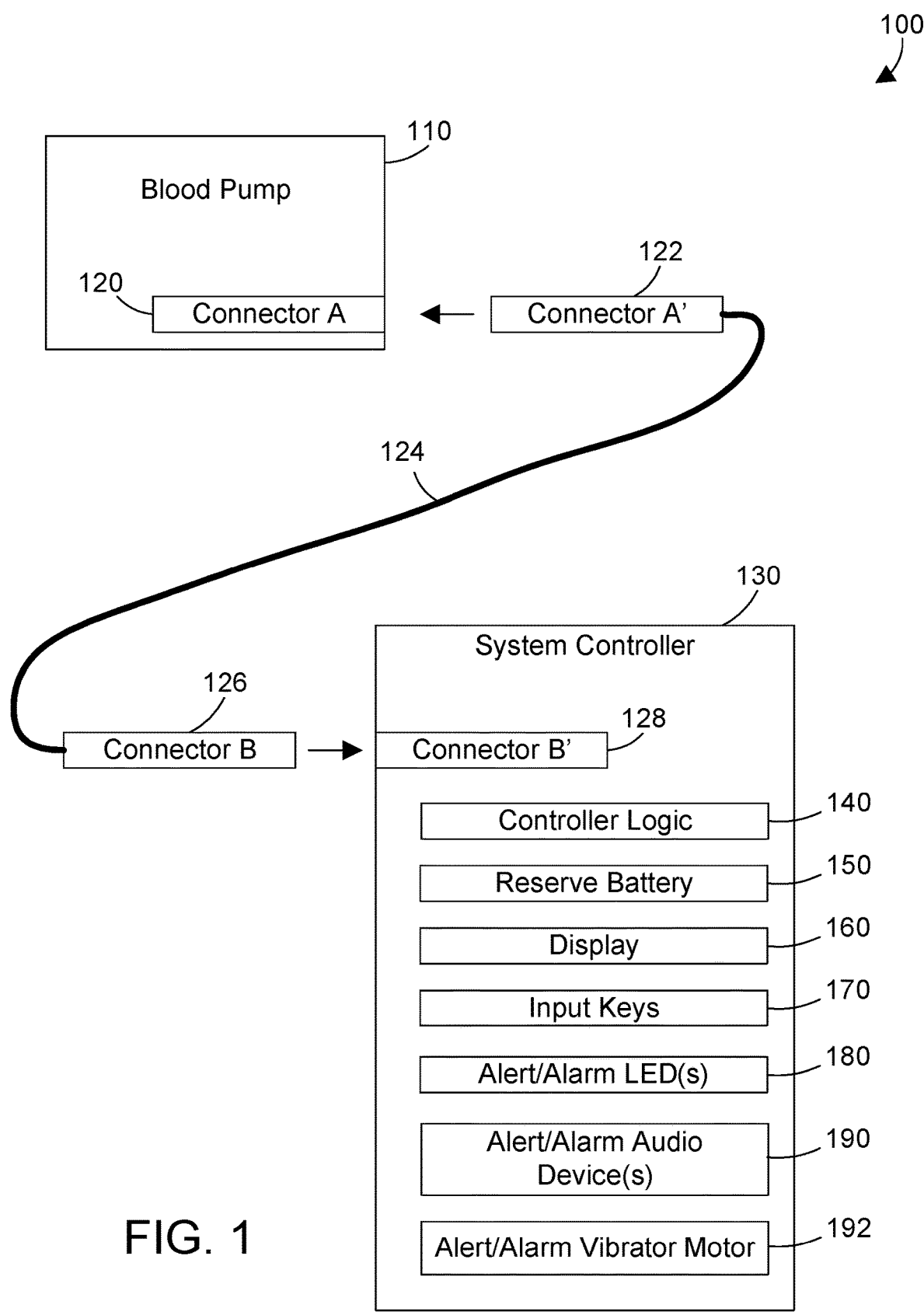
FIG. 1 is a block diagram of a system that includes a blood pump, cable and system controller.

Referring to FIG. 1, a blood pump system 100 is shown that includes a blood pump 110 a cable 124, and a system controller 130. The blood pump 110 can be an implantable blood pump. A ventricular assist device (VAD) is one suitable embodiment for blood pump 110. Blood pump 110 preferably includes an impeller sealed within a pump housing and hydrodynamically suspended in the pump housing. The impeller includes a plurality of magnets, and the blood pump has a plurality of stator coils in a brushless DC motor that, when driven by a plurality of drive signals, make the impeller rotate within the pump housing.

The blood pump 110 includes a connector 120 that receives a mating connector 122 on cable 124. Applicant has developed medical connectors suitable for use with implanted devices such as pacemakers and blood pumps, as shown and described in the following U.S. Pat. Nos. 10,480,690; 10,741,968; 10,833,451; 10,855,026; 10,886,663; and 11,309,662. Connectors 120 and 122 could be connectors as shown in these listed patents, or could be any other suitable type of connector. In one specific embodiment the cable 124 is a percutaneous cable that connects to a blood pump 110 that is implanted in a patient's body, passes through the skin, and connects to an external controller, such as system controller 130. Cable 124 includes a suitable connector 126 that mates with a corresponding connector 128 in the system controller so the system controller 130 can provide the drive signals to the stator coils in the brushless DC motor in the blood pump 110.

As shown in FIG. 1, the system controller 130 preferably includes controller logic 140; a reserve battery 150; a display 160; one or more input keys 170; one or more LEDs 180 for alerts and/or alarms; one or more audio devices 190 for alerts and alarms; and an alert/alarm vibrator motor 192 for providing haptic notice of alerts and alarms. The controller logic 140 monitors the function of the brushless DC motor in the blood pump 110 and provides suitable drive signals to the stator coils in the brushless DC motor so the blood pump 110 operates at a desired speed. The reserve battery 150 is internal to a housing for the system controller 130, and provides power when external power sources, such as a primary battery or an AC/DC adapter, are not plugged in or do not provide power to the system controller 130. The display 160 can be any suitable type of display. In the most preferred implementation, display 160 is a low-power liquid-crystal display (LCD). Input keys 170 are provided to provide user input to the system controller. Input keys could include, for example, a mute key that mutes an audio device when the audio device indicates an alert, and a "Next" key that allows advancing from the current screen to a next screen in a multi-screen message. The LEDs 180 are used to provide a visual indication of alerts or alarms detected by the system controller 130. For example, LED(s) 180 could provide a slow yellow flashing signal in the event of an alert and could provide a fast red flashing signal in the event of an alarm. The audio device(s) 190 are used to provide an audio indication of alerts or alarms detected by the system controller 130. For example, audio device(s) 190 could provide a slow, soft beep in the event of an alert and could provide a fast, loud beep in the event of an alarm.

Figure 2:
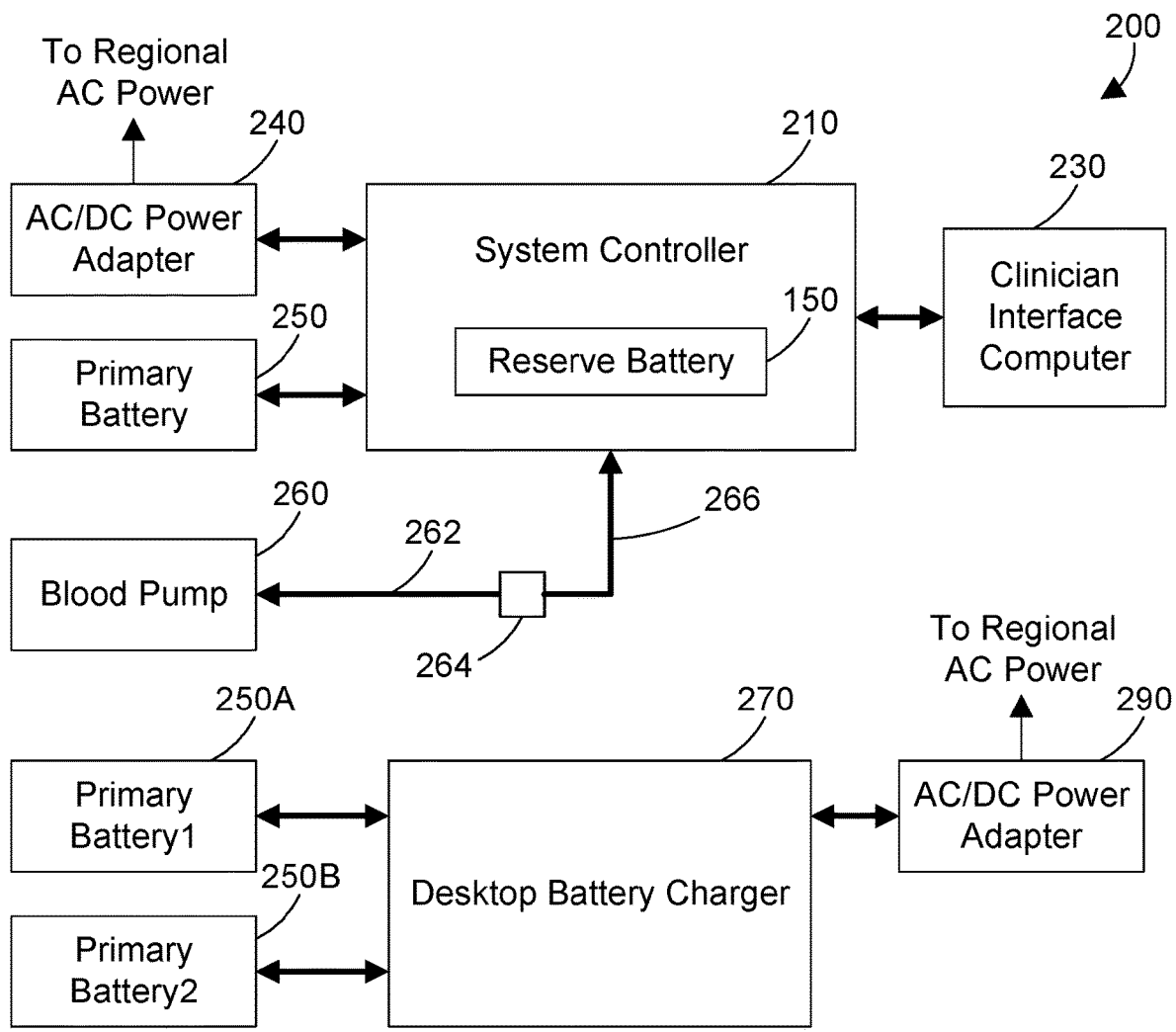
FIG. 2 is a block diagram showing the system with additional details according to a preferred embodiment.

The blood pump system disclosed and claimed herein could also include other components, as shown in system 200 in FIG. 2. System controller 210 in FIG. 2 is one suitable example of system controller 130 in FIG. 1, and blood pump 260 is one suitable example of blood pump 110 in FIG. 1. System controller 210 includes the internal reserve battery 150 as discussed above. The system controller 210 further includes a clinician interface that allows connecting a clinician interface computer 230 to the system controller 210. A medical clinician can use the clinician interface computer 230 to set the speed of the blood pump in the system controller 210, and to also define or select various alert and alarm conditions. The system controller 210 includes a blood pump interface for receiving a cable 266 that connects to the blood pump 260. The system controller 210 is outside a human body and can connect to a suitable connector 264 that connects to a percutaneous cable 262 to an implanted blood pump 260. Of course, the blood pump 260 could be outside a human body as well, with percutaneous tubes that connect to blood vessels inside the human body. Note the connector 264 could be used to plug in an extension cable that would allow the system controller to be farther from the patient. This would be helpful, for example, if the patient needed to undergo surgery.

The system controller 210 also includes an interface to a primary battery 250 and to an AC/DC power adapter 240 that receives power from a regional alternating-current (AC) power source. In a preferred embodiment, the system controller 210 preferably does not include circuitry for charging the primary battery 250. The primary battery 250 is removably coupled to an exterior of the housing of the system controller such that the primary battery 250 can be removed from the system controller and connected to the desktop battery charger 270 when the primary battery 250 needs to be recharged.

The system controller 210 uses a power hierarchy to determine which power source to apply to run the system controller 210. When the AC/DC power adapter 240 is plugged into the regional AC power and is plugged into the system controller 210, the AC/DC power adapter 240 provides power to the system controller 210. When the primary battery 250 is plugged in to the system controller 210 and the AC/DC power adapter 240 is not plugged in to the system controller 210, or is plugged into the system controller 210 but is not providing power, such as during a power outage, the primary battery 250 provides power to the system controller 210. When neither the AC/DC power adapter 240 nor the primary battery 250 are providing power to the system controller 210, the system controller is powered by the reserve battery 150. This configuration provides for safety and convenience. When a patient connected to the blood pump is going to be in one place for a while, the patient can use the system controller 210 in a tethered mode and plug the AC/DC power adapter into the wall receptacle and into the system controller 210, thereby not draining the primary battery 250 or the reserve battery 150. When the patient no longer wants to be tethered to the AC/DC power adapter 240, the patent can unplug the AC/DC power adapter 240 so the patient can use the system controller 210 in an untethered mode where the relatively large primary battery 250 can provide power to the system controller 210 for several hours before needing to be recharged. When the primary battery 250 is nearly discharged and needs to be charged, the patient can disconnect the primary battery 250 from the system controller 210 and connect a different primary battery to the system controller 210. While the primary battery 250 is disconnected, the system controller 210 is powered by the reserve battery 150. The reserve battery 150 that is internal to the housing of the system controller 210 thus provides power to assure the blood pump 260 continues to run even when both the AC/DC power adapter 240 and primary battery 250 are both disconnected. In normal use, the system controller 210 will only be powered by the reserve battery for the small amount of time it takes the user to disconnect a discharged primary battery and replace it with a charged primary battery. The reserve battery 150 is preferably a lithium-ion rechargeable battery, and system controller 210 includes a charging circuit that keeps the reserve battery 150 charged when the system controller 210 is connected to the AC/DC power adapter 240 or to the primary battery 250. The primary batteries used with the system controller 210, such as primary battery 250, 250A and 250B in FIG. 2, are preferably rechargeable lithium-ion batteries.

The desktop battery charger 270 receives power from an AC/DC power adapter 290 coupled to regional AC power. The desktop battery charger 270 can charge multiple primary batteries at one time. For the specific example in FIG. 2, desktop battery charger 270 can charge two primary batteries 250A and 250B at the same time. Of course, other configurations for the desktop battery charger could charge greater or fewer primary batteries as needed. In the most preferred embodiments, the system controller 210 includes a latch system for mechanically and electrically attaching the primary battery 250 to the housing of the system controller 210, and the desktop battery charger 270 also provides an identical or similar latch system so the primary battery attaches to the desktop battery charger 270 in the same way that it attaches to the system controller. This provide ease of use, where the user can get accustomed to connecting and disconnecting the primary battery on the system controller and this same method and procedure can be used to connect and disconnect primary batteries to the desktop battery charger. The desktop battery charger 270 can use any suitable charging method to charge the primary batteries. In a preferred embodiment, the desktop battery charger 270 can recharge a primary battery in approximately three hours.

Figure 3:
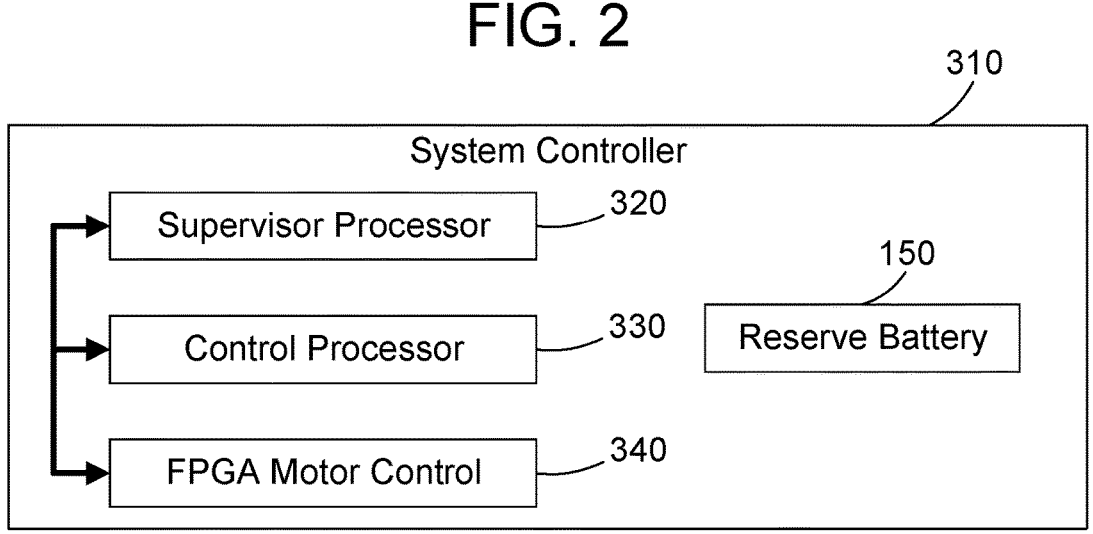
FIG. 3 shows components of the system controller in a preferred embodiment.

Referring to FIG. 3, a system controller 310 is one suitable embodiment for system controller 130 shown in FIG. 1 and for system controller 210 shown in FIG. 2. System controller 310 includes a reserve battery 150 internal to the housing of the system controller, as discussed above with reference to system controller 130 in FIG. 1 and system controller 210 in FIG. 2. The controller logic 140 in FIG. 1 can include as shown in FIG. 3 a supervisor processor 320, a control processor 330, and a programmable logic device to provide motor control, such as FPGA motor control 340. Separation of the functions of the system controller into the three blocks 320, 330 and 340 shown in FIG. 3 provides significant advantages. First, control processor 330 is a microcontroller that provides the needed management functions for the system controller 310, including the monitoring of alerts and alarms, outputting to the display, receiving input from a user via the input keys 170, performing power switching between power sources, etc. The FPGA motor control 340 is a field-programmable gate array (FPGA) that has been programmed to provide sensorless field-oriented control (SFOC) of a brushless DC motor in a blood pump. By dedicating control of the blood pump to the FPGA motor control 340, the blood pump will continue to run and be controlled by the FPGA motor control 340 even if or when the control processor 330 stops working. Thus, even when the control processor 330 ceases to function correctly, the FPGA motor control 340 will continue to function and control the blood pump because the FPGA motor control is implemented in hardware that is not dependent on the function of the control processor 330 to function properly. In addition, the FPGA motor control 340 functions according to electronic clocks as opposed to using software that can have variable timing. The FPGA motor control 340 can thus control very high-speed motors that would be difficult to control via a processor running software. The FPGA motor control 340 is also a dedicated, sole-function circuit, with no extraneous or other features that could cause it to fail. In addition, the FPGA could have space for expansion to add other dedicated hardware functions to the system controller, such as: a Medical Implant Communication Services (MICS) interface or Bluetooth communication interface from and with an implanted controller for external parameter programming; an interface to a microelectromechanical systems (MEMS) pressure sensor circuit for flow measurement; and an interface to a transcutaneous battery charging system.

While sensorless field-oriented control (SFOC) of a brushless DC motor is known in general, this method has not been used for blood pumps. SFOC provides a significant number of advantages compared to the known art for blood pumps. Blood pumps need to run at a relatively high speed of thousands or tens of thousands of RPM, with a variation of no more than 100 RPM. SFOC allows more precise motor control because it provides the spinning rotor (or impeller) exact position (rotor angle). SFOC is a closed-loop design, as opposed to known drive systems for blood pumps. With precise rotor position, the spin rate, or speed, is known, and the field in the stator can be driven to produce maximum torque. This is the essential difference SFOC provides in controlling brushless DC (BLDC) motors versus other motor drive mechanisms. The rotor position and speed are not known with inductive motors or motors run with other open-loop controls, like trapezoidal or sinusoidal drive. With open-loop systems, the actual rotational speed of the rotor (impeller) is only an estimate. With SFOC, the rotational speed can be measured.

SFOC also increases power use efficiency, reducing power consumption when compared with trapezoidal drive or sinusoidal drive methods for the same motor design. This is because the SFOC algorithm optimizes the pump motor torque. The energy sent into the phase coils of the stator creates a magnetic field that is always in the exact position to spin the rotor with the maximum force. There is minimal wasted energy from not having the magnetic field in the phase coils driving the rotor in anything less than the precise position relative to the rotor's permanent magnetic field. The increased power use efficiency results in reduced power consumption, reduced heat generation, and reduced size for the system controller. In addition, the increased power use efficiency allows a smaller reserve battery to be used, or allows a larger reserve battery to last longer.

The SFOC method of driving the pump motor also reduces torque ripple. Torque ripple is also the result of not having the magnetic field in the stator in the best position to cause the rotor only to spin. If the stator field lags or leads the best position relative to the rotor field, then the rotor slows and or is knocked away from its central axis. The rotor wobbles more without SFOC. SFOC reduces this torque ripple (rotor speed stutter and wobble) significantly because the SFOC algorithm tries to drive the axial displacement parameter towards zero and smooths the torque value. The result of reducing torque ripple is longer bearing life in the motor, and potentially better protection against hemolysis.

SFOC also allows using the motor itself as a sensor, because the rotor position gives precise speed, and measuring motor current is useful for flow measurement and detecting obstructions. SFOC is "sensorless" because there are no independent sensors, such as Hall-effect sensors for detecting rotor speed, mechanical load sensors, or separate governor circuits. The current sensors used by the SFOC algorithm to perform the motor control can also sense load changes affecting the motor. Thus, measured variables, current sense values, torque ripple, and the programmed speed can be used to estimate flow through the pump and to detect obstructions in the flow.

SFOC uses three-dimensional geometry to convert back and forth between a rotating reference and a fixed reference and between voltages that induce currents and currents that indicate voltages. SFOC has been implemented in software in the past, but running SFOC in a software-controlled environment requires a very high-speed microcontroller. Suppose a program in a microcontroller simultaneously performs calculations for a SFOC loop spinning a pump motor and also runs other software that performs other functions, such as monitoring batteries, logging motor control events, displaying messages on an LCD, generating alarms, communicating over USB, etc. In that case, the timing of the SFOC algorithm might very possibly be disturbed by the operations of the other software. SFOC requires exact timing. Software systems are inherently not capable of precise timing under all circumstances. Failure to operate correctly in one part of a software system can affect other operating software parts. For this reason implementing SFOC in an FPGA provides independence from the microcontroller performing other functions, which assures the blood pump will continue to function even if or when the microcontroller fails. In addition, the FPGA implementation for SFOC disclosed and claimed herein provides very accurate high-speed hardware timers, thus assuring very high-speed control of the blood pump motor. Once the speed for the pump motor is set in the FPGA motor control 340, the pump motor spins at precisely that speed, no matter what the supervisor processor 320 or control processor 330 are doing, and regardless of whether either or both of these processors 320 and 330 have failed. This allows the control processor to fault, lock-up, or halt for no reason, all while the FPGA motor control 340 continues to spin the pump motor at precisely the programmed speed. In addition, the control processor could be intentionally stopped so its software can be updated, all while the FPGA motor control 340 continues to spin the pump motor at precisely the programmed speed. Once the pump motor speed setting is set in the FPGA motor control 340, all the FPGA motor control 340 needs to continue spinning the pump motor at the set speed setting is uninterrupted power.

Because the system controller 310 controls a vital, life-supporting device, namely a blood pump, failure of the system controller 310 can cause injury or death. For this reason, a supervisor processor 320 is provided to independently monitor the function of the control processor 330 and FPGA motor control 340. Even if the control processor 330 fails, which would render the control processor 330 incapable of alerting the user of the failure, the supervisor processor 320 will detect the failure of the control processor 330, and can provide needed alerts and/or alarms. In one suitable embodiment, the control processor 330 could send periodic heartbeat messages to the supervisor processor 320, and as long as the supervisor processor 320 receives the heartbeat messages within a defined timeframe, the supervisor processor can assume the control processor 330 is functioning correctly. The heartbeat messages could be sent, for example, via a universal asynchronous receiver/transmitter (UART) channel between the control processor 330 and the supervisor processor 320. Note, however, that supervisor processor 320 has other ways besides monitoring a heartbeat from the control processor 330 to determine when something is wrong in the system controller 310. For example, the supervisor processor 320 can independently monitor parameters of the FPGA motor circuit 340 to determine whether speed of the blood pump is what it should be. Regardless of the source of failure, when the supervisor processor 320 detects a failure in the system controller, whether in the control processor 330 or in the FPGA motor control 340, the supervisor processor 320 can provide an alert and/or alarm that will let the user know what the user needs to do to fix the problem, which may be to replace the defective system controller with a different system controller that functions properly.

The supervisor processor 320 could be a microcontroller, or could be a simple state machine or other combination of hardware/software. The supervisor processor 320 can be any suitable entity that is capable of monitoring the control processor 330 and the FPGA motor control 340.

Figure 4:
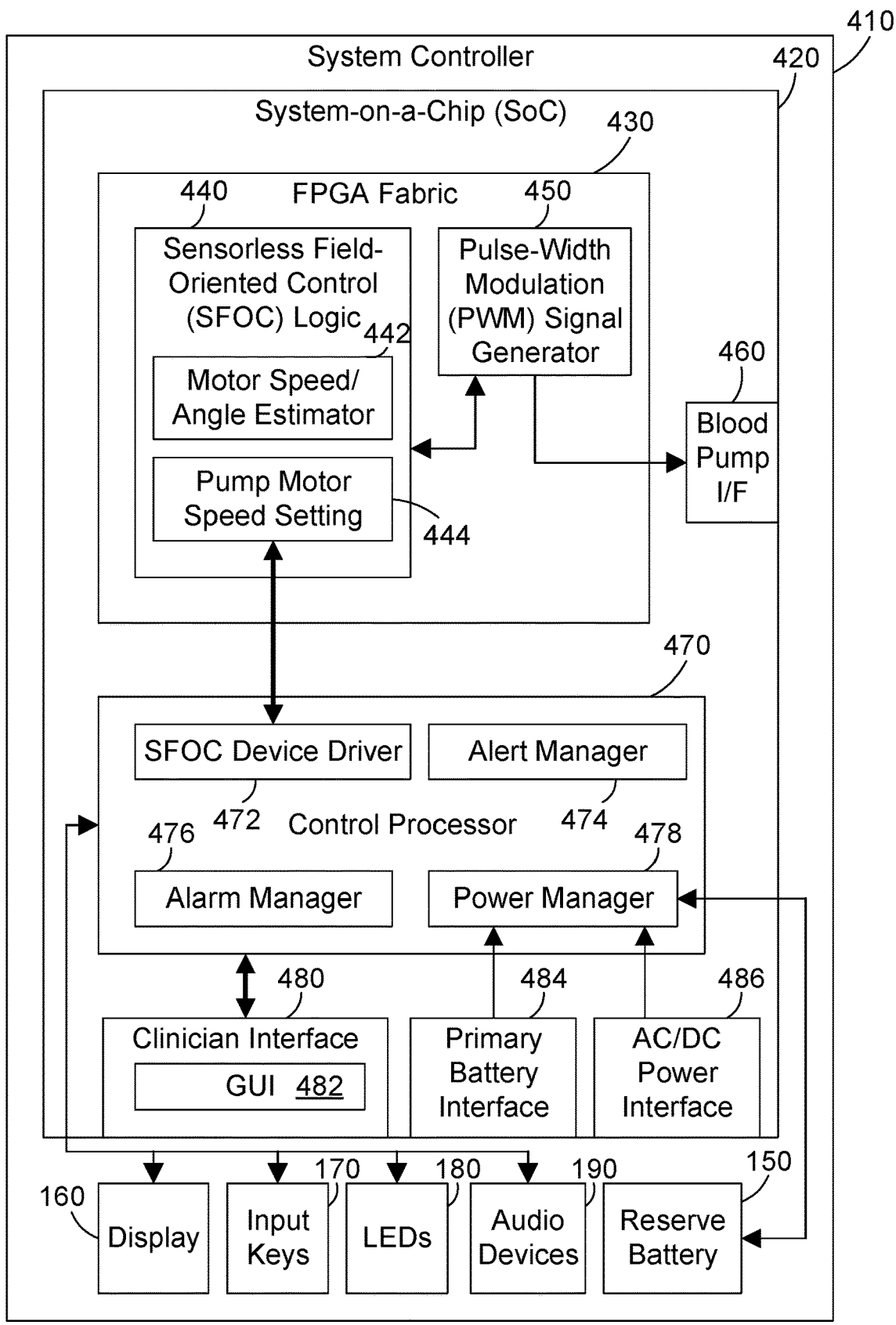
FIG. 4 is a block diagram showing some parts of the system controller implemented on a System-on-a-Chip (SOC)

In a preferred embodiment, both the control processor 330 and the FPGA motor control 340 can be implemented as a system-on-a-chip (SoC). A suitable example of such a SoC implementation is shown in FIG. 4. The system controller 410 in FIG. 4 is one suitable implementation for system controllers 130 in FIG. 1, 210 in FIGS. 2 and 310 in FIG. 3. System controller 410 includes a system-on-a-chip (SoC) 420. The SOC 420 includes an FPGA fabric 430; a control processor 470; a clinician interface 480; a primary battery interface 484; and an AC/DC power interface 486. The FPGA fabric 430 is one suitable embodiment of the FPGA motor control 340 shown in FIG. 3. The FPGA fabric 430 implements sensorless field-oriented control (SFOC) logic 440 and a pulse-width modulation (PWM) signal generator 450 that provides drive signals for stator coils in the brushless DC motor in the blood pump via the blood pump interface 460. The SFOC logic 440 includes a motor speed and position estimator 442 and a pump motor speed setting 444. The motor speed/angle estimator 442 preferably estimates both motor speed and angle. The pump motor speed setting 444 is most preferably written to the SFOC logic 440 by a SFOC device driver 472 in the control processor 470 as a result of receiving input from a clinician that sets the pump motor speed via the clinician interface 480. The clinician interface 480 preferably includes a graphical user interface (GUI) 482 that allows the clinician to interact with the system controller 410 when a clinician computer system is coupled to the clinician interface 480. The control processor 470 additionally includes an alert manager 474, an alarm manager 476 and a power manager 478. The functions of the alert manager 474 and alarm manager 476 could be combined. The functions of the alert manager 474, the alarm manager 476 and the power manager 478 are discussed in more detail below. The control processor 470 on the SOC 420 is also coupled to a reserve battery 150, display 160, one or more input keys 170, one or more LEDs 180 and one or more audio devices 190 as discussed above. The SOC implementation shown in FIG. 4 provides an efficient and low-cost implementation for controlling the function of the blood pump.

Figure 5:
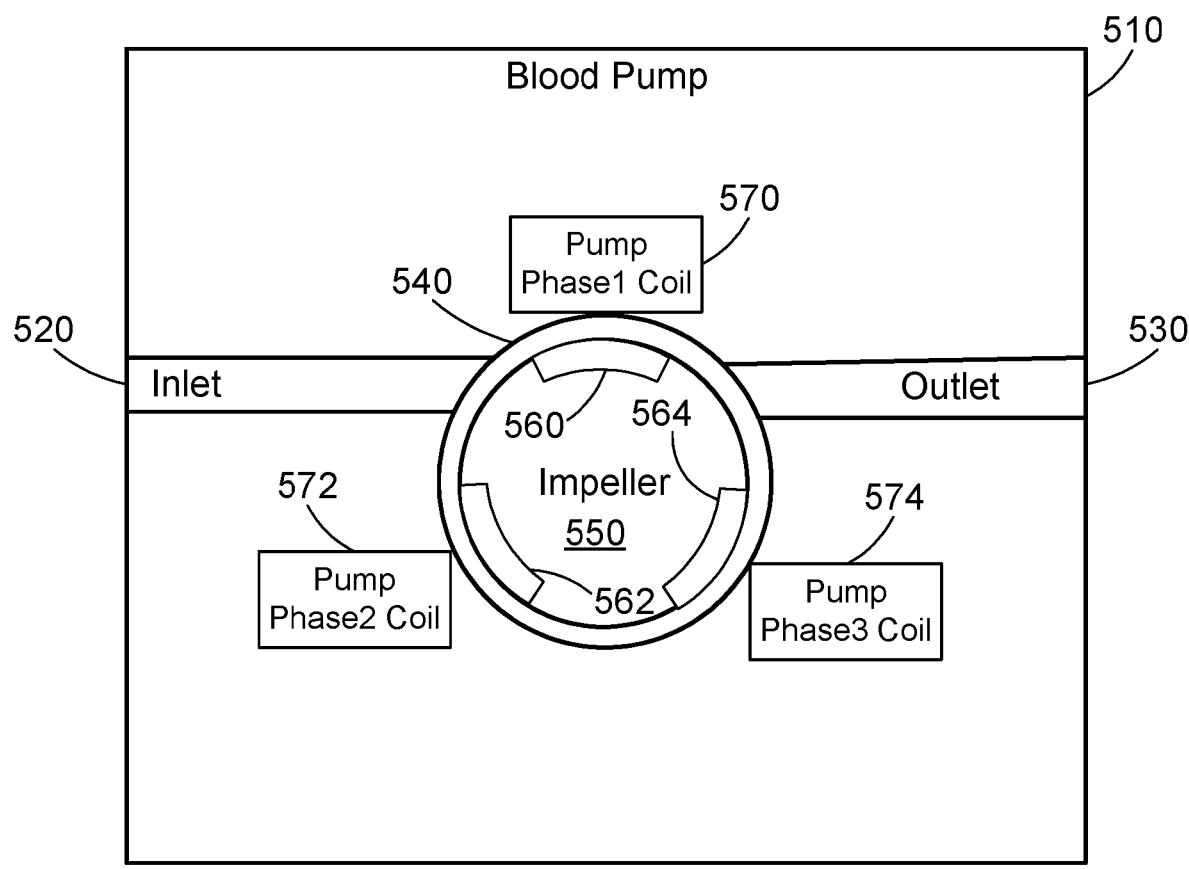
FIG. 5 is a block diagram of a blood pump according to a preferred embodiment.

A block diagram of a blood pump 510 is shown in FIG. 5. Blood pump 510 is one suitable embodiment for blood pump 110 in FIG. 1. Blood pump 510 includes an inlet 520, a pump chamber 540, and an outlet 530. Inlet 520 is connected to a blood vessel from which blood needs to be pumped. Outlet 530 is connected a blood vessel into which blood needs to be pumped. Said another way, the inlet 520 is the low pressure port and the outlet 530 is the high pressure port. The pump chamber 540 is sealed, and an impeller 550 within the pump chamber 540 is hydrodynamically suspended within the pump chamber 540. This means there is no shaft or other mechanical connection from the impeller to drive the impeller. The impeller includes a plurality of magnets. In the specific embodiment in FIG. 5, three magnets 560, 562 and 564 are shown. There could be more magnets than the three shown in FIG. 5 within the scope of the preferred embodiments. FIG. 5 also shows multiple pump phase coils 570, 572 and 574 that are used to drive the impeller. The coils 570, 572 and 574 are stator coils that are part of the drive portion of a brushless DC motor in the blood pump. In the most preferred embodiment, the pump phase coils 570, 572 and 574 are wired as a standard 3-phase motor in a wye topology. The system controller provides drive signals to the pump phase coils 570, 572 and 574 that are pulse-width modulated (PWM) voltages. The PWM voltages create near-sinusoidal currents that generate electromagnetic fields that act on the magnets on the impeller causing the impeller to rotate and pump blood.

Figure 6:
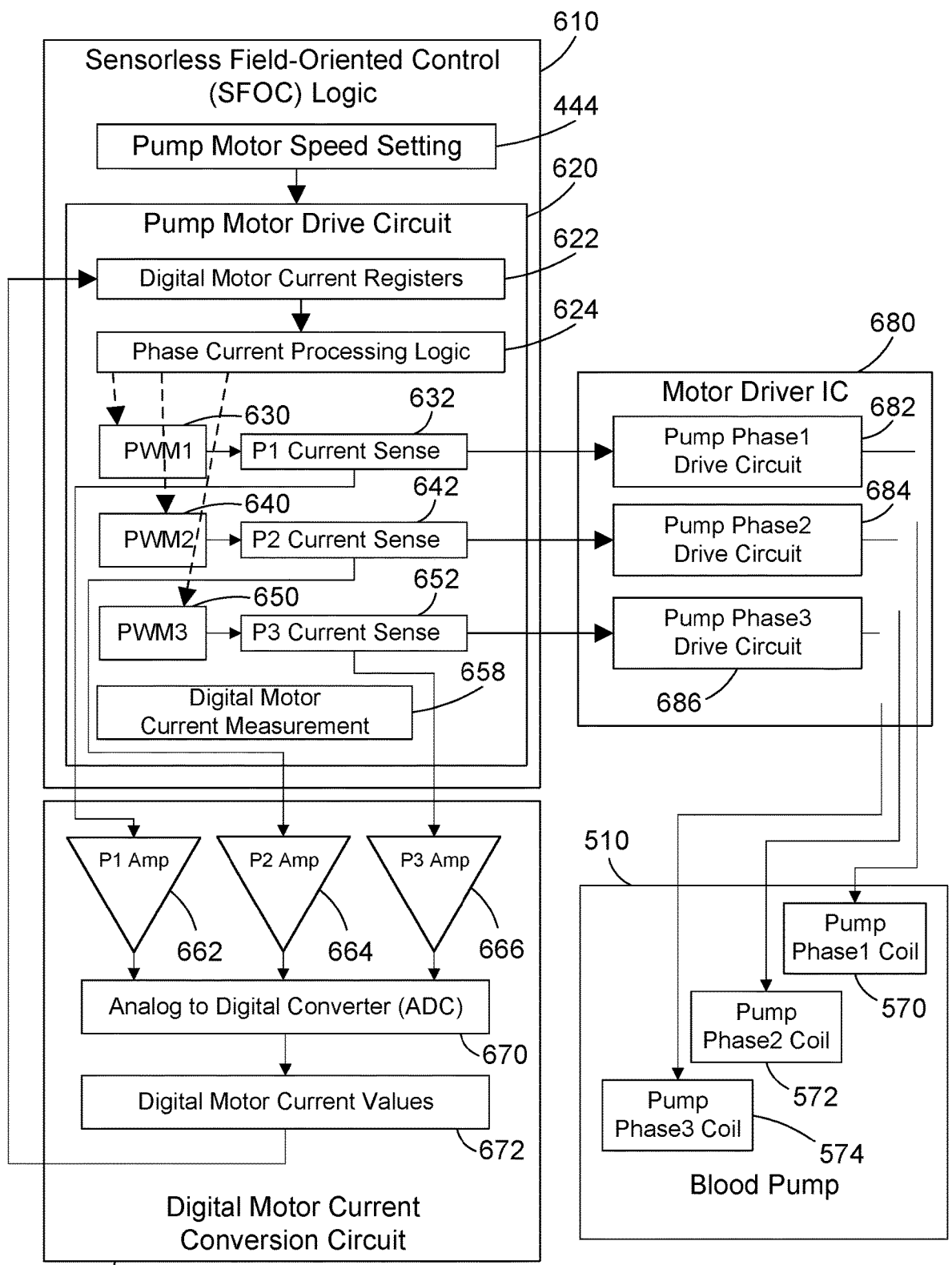
FIG. 6 is a block diagram showing how the system controller drives stator coils which provides an estimate of blood flow through the blood pump.

Referring to FIG. 6, SFOC logic 610 is one suitable embodiment for the SFOC logic 440 shown in FIG. 4. The SFOC logic 610 includes the pump motor speed setting 444 shown in FIG. 4 and discussed above. The pump motor speed setting 444 is preferably set by a clinician via the clinician interface. The pump motor drive circuit 620 includes digital motor current registers 622 that contain the values of digital motor current, discussed in more detail below. The digital motor current values in the digital motor current registers 622 are processed by the phase current processing logic 624. The result is a PWM for each phase of the blood pump motor. Thus, for a three-phase blood pump motor, digital current processing logic generates PWM1 630, PWM2 640 and PWM3 650. These are pulse-width modulated signals that drive the motor driver integrated circuit 680. Each phase has a current sense from which current can be determined. Thus, phase 1 has a P1 current sense 632; phase 2 has a P2 current sense 642; and phase 3 has a P3 current sense 652. In a preferred embodiment, the current senses 632, 642 and 652 are resistors inline such that voltage across the current sense resistor is proportional to the current provided in each phase.

A digital motor current conversion circuit 660 provides conversion of the sensed currents to motor current values under control of a digital motor current measurement circuit 658. The voltage from each current sense element needs to be amplified, so there are three amplifiers 662, 664 and 666 that amplify the voltage from their corresponding current sense elements 632, 642 and 652. The amplified signals are input to an analog-to-digital converter (ADC), which generates therefrom under control of the circuit 658 digital motor current values 672. These digital motor current values 672 are written to the digital motor current registers 622, creating a closed-loop system for controlling the blood pump motor.

In the specific embodiment shown in FIG. 6, the PWM signals 630, 640 and 650 do not have sufficient voltage to drive the pump phase coils directly, so they are input into a motor driver integrated circuit 680, which then generates from each PWM signal a corresponding drive signal for the three phase coils. Thus, pump phase1 drive circuit 682 drives pump phase1 coil 570 in the blood pump 510; pump phase2 drive circuit 684 drives the pump phase2 coil 572; and pump phase3 drive circuit 686 drives the pump phase3 coil 574.

Figure 7:
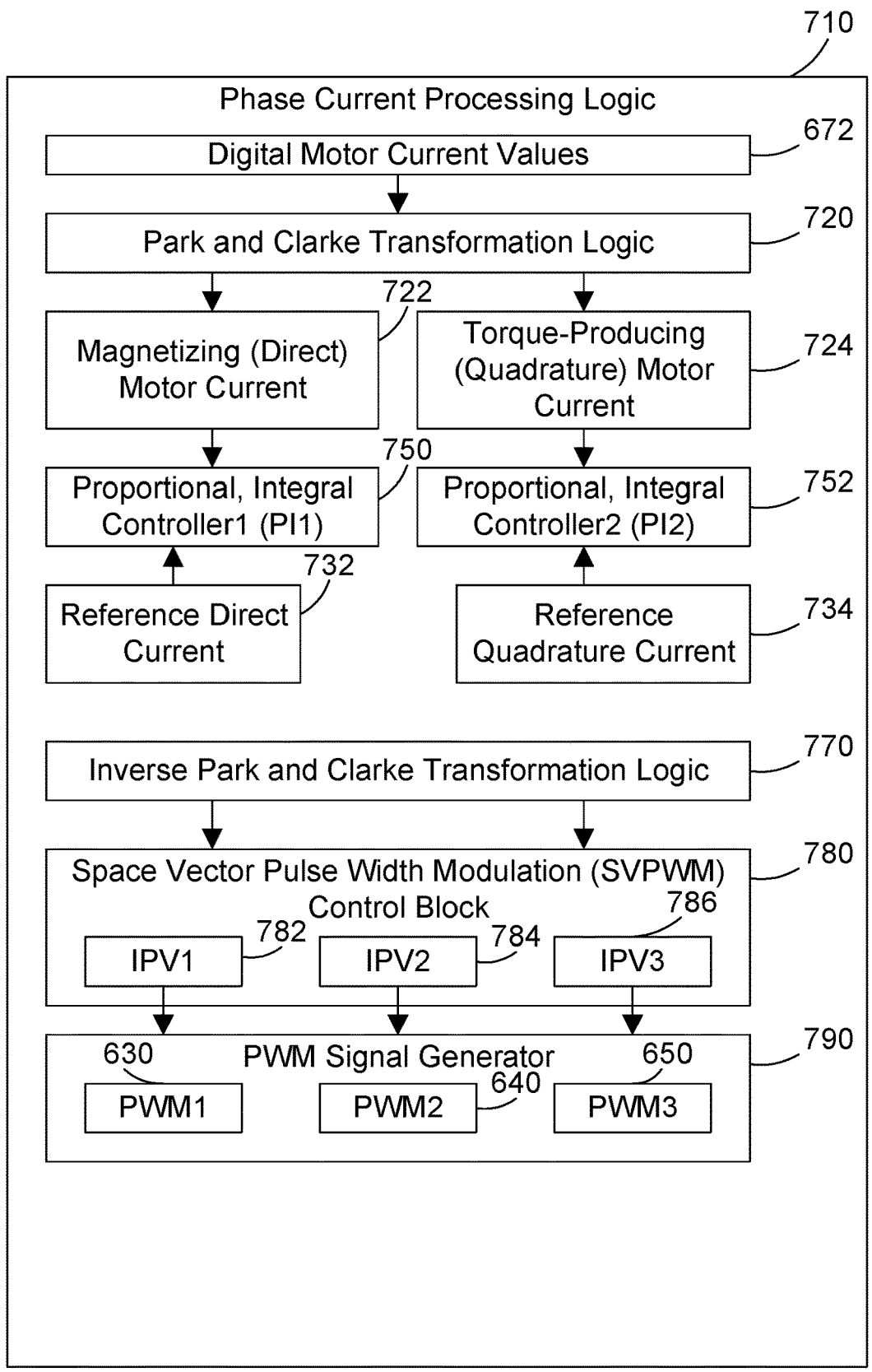
FIG. 7 is a block diagram showing one suitable implementation for the digital current processing logic shown in FIG. 6.

One specific implementation for the phase current processing logic 624 shown in FIG. 6 is shown at 710 in FIG. 7. The digital motor current values 672 undergo a Park and Clarke transformation by Park and Clarke transformation logic 720, which generates both the magnetizing (direct) motor current 722 and the torque-producing (quadrature) motor current 724. A first proportional, integral (PI) controller 750 then compares the magnetizing (direct) motor current 722 with a reference direct current 732 to generate a direct error signal. In the most preferred implementation, the reference direct current 732 has a value of zero. In similar fashion, a second PI controller 752 compares the torque-producing (quadrature) motor current 724 with a reference quadrature current 734 to generate a quadrature error signal. The reference quadrature current 734 is preferably computed from the desired speed reference and the motor's physical parameters. These signals are then processed by inverse Park and Clarke transformation logic 770 and input to a space vector pulse width modulation (SVPWM) control block 780 to generate a magnetizing (direct) PWM duty cycle and a torque-producing (quadrature) PWM duty cycle. The SVPWM control block 780 averages the minimum and maximum of each phase voltage and a resulting voltage offset is calculated, which is subtracted from each of the instantaneous phase voltages. The output of the SVPWM control block 780 are three third-harmonic injected phase voltages IPV1 782, IPV2 784, and IPV3 786. The phase voltage 782, 784 and 786 are input to the PWM signal generator 790, which inserts dead time and supports either edge-aligned or center-aligned pulse width modulation. The PWM signal generator 790 generates three pulse width modulated signals PWM1 630, PWM2 640, and PWM3 650, which are then used to generate the drive signals for the blood pump motor phases, as shown in FIG. 6.

Figure 8:
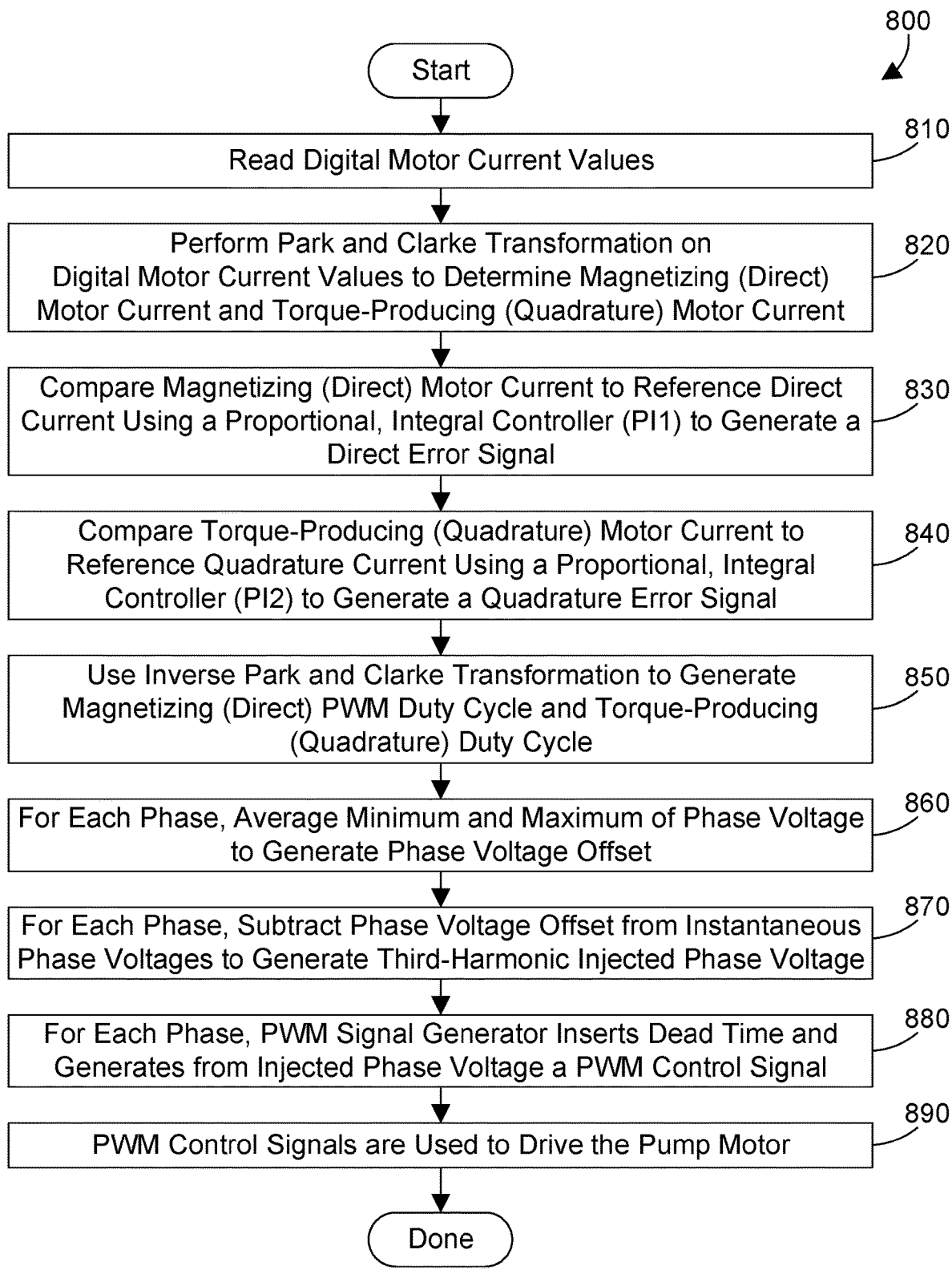
FIG. 8 is a flow diagram of one suitable method for generating drive signals for the blood pump motor.

FIG. 8 shows a method 800 that is preferably performed by the phase current processing logic 710 shown in FIG. 7. The digital motor current values are read (step 810). Next, perform Park and Clarke transformation on the digital motor current values to determine magnetizing (direct) motor current and torque-producing (quadrature) motor current (step 820). Compare the magnetizing (direct) motor current to a reference direct current using a proportional, integral controller PI1 to generate a direct error signal (step 830). Compare the torque-producing (quadrature) motor current to a reference quadrature current using a second PI controller PI2 to generate a quadrature error signal (step 840). Use inverse Park and Clarke transformation to generate magnetizing (direct) PWM duty cycle and torque-producing (quadrature) duty cycle (step 850). For each phase, average the minimum and maximum of phase voltage to generate a phase voltage offset (step 860). For each phase, subtract the phase voltage offset from the instantaneous phase voltages to generate third-harmonic injected phase voltage (step 870). For each phase, the PWM signal generator inserts dead time and generates from the injected phase voltage a PWM control signal (step 880). The PWM control signals are then used to drive the blood pump motor (step 890). Method 800 is then done.

Figure 9:
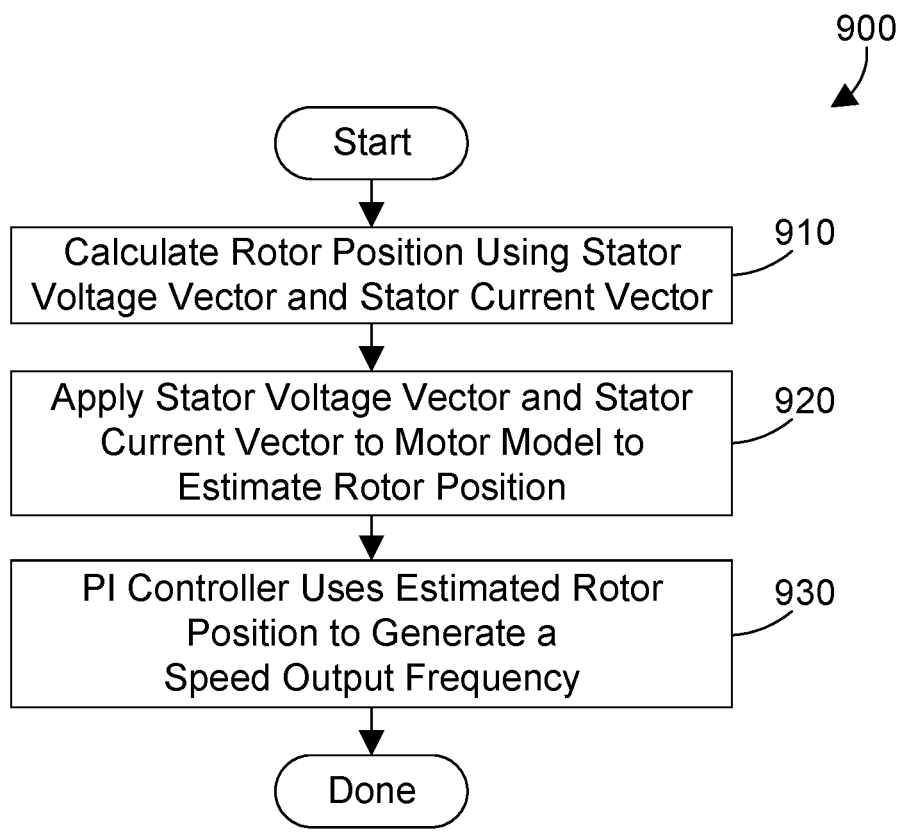
FIG. 9 is a flow diagram of a method for determining speed of the blood pump motor.

Referring to FIG. 9, a method 900 is preferably performed by the motor speed/angle estimator 442 in FIG. 4. ? The rotor position is calculated using the stator voltage vector and the stator current vector (step 910). The stator voltage vector and stator current vector are then applied to a motor model to estimate the rotor position (step 920). A PI controller then uses the estimated rotor position to generate a speed output frequency (step 930). The speed output frequency is then displayed on the system controller display (step 940).

Figure 10:
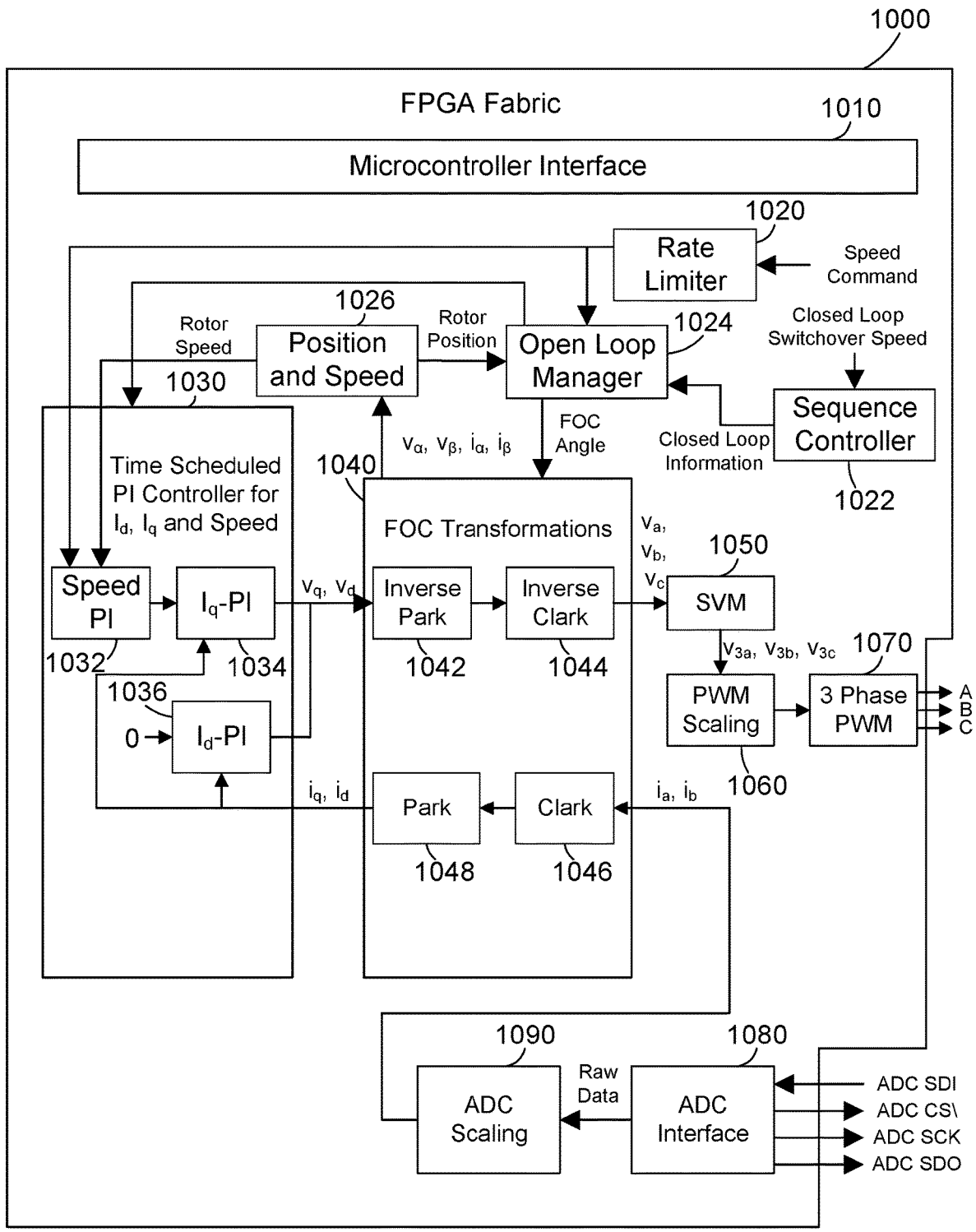
FIG. 10 is a block diagram of one specific implementation for the FPGA motor control within the system controller shown in FIG. 3 that provides the field-oriented control for the blood pump motor.

One specific implementation for the FPGA motor control 340 in FIG. 3 and the FPGA fabric 430 in FIG. 4 is shown at 1000 in FIG. 10. The FPGA fabric 1000 includes a microcontroller interface 1010 that allows the control processor to write values to registers in the FPGA fabric 1000. To understand the function of the circuitry in FIG. 1000, some additional information regarding control of BLDC motors using Field Oriented Control (FOC) is described below.

Brushless Direct Current (BLDC) motors have a magnetized rotor and an energized stator to make the motor run. The rotor is the "rotating" part inside the motor core. In the preferred embodiments, the pump impeller itself is the actual physical rotor. Spinning the impeller pumps the blood into the pump inlets and out through the axial flow output. The stator is the stationary, "fixed" part of the BLDC motor. It consists of three (3) wire coils (phases) with each coil wound in an orientation tangential to three points oriented 120 degrees apart around the outside of the motor. When the motor control system sends voltage signals, which are waveforms of changing voltages, through the stator coils, changing currents generated in the phase coils by these changing voltages produce changing magnetic fields around the coils. The magnetic fields induced by currents flowing through the phase coils will thus have their poles pointing along a line through motor's central axis.

The Field-Oriented-Control (FOC) algorithm measures phase currents and controls phase voltages using these phase current measurements. FOC is a closed-loop system design.

Each of the three phases of a BLDC Motor is oriented at 120 degrees rotated relative to one another, and spaced evenly around the motor's circumference. Each individual coil, when energized by a changing voltage signal, produces a current and induces an associated magnetic field of a specific magnitude, which is always aligned perpendicular to the coil, with one magnetic pole (North or South) toward and the other directly away from the central axis of the motor core. This gives a geometric understanding of the three magnetic fields created in the three ABC phase coils.

The combined magnitudes and N-S directions (polarity) of the three magnetic forces (the three magnetic field vectors) produced in individual coils create together a magnetic field of a specific strength (magnitude) and with a particular North-South pole orientation (direction) across and within the motor core. The magnetic field produced in the stator is always oriented across and through the rotational axis of the motor.

The rotor has at least one set of alternating N-S-N-S . . . magnetic pole pairs around its circumference. A pole pair on the rotor orients across the rotor's rotational axis (North and South poles on opposite rotor sides). The rotor moves (rotates) because its magnetic pole pairs are attracted to the opposing poles (N to S and S to N) of the rotating combined magnetic field produced by the coils in the stator.

The FOC control algorithm creates magnetic fields in the stator by sending rapidly changing voltage waveform signals into the motor's stator phase coils. The changing voltage waveforms cause alternating current flows in the stator coil wires and produce rapidly changing magnetic fluxes within the stator. Correct operation of the FOC algorithm energizes only two phases of the stator at any one time, with a positive voltage (and positive current) in one phase coil, and a negative voltage (and negative current) in another opposing phase, thus producing opposing North and South magnetic fluxes on opposite sides of the motor core at all times. The rotor moves to align its magnetic pole pairs (N-S) opposite the continuously rotating combined magnetic field produced in the energized stator coils. The FOC algorithm sends independent and precisely coordinated voltage waveforms through the stator coils, which generate a rotating magnetic field inside the motor with the magnetic field directed across the motor core. The rotating magnetic field attracts the rotor poles and spins the rotor along with the rotating field.

The main objective of the computations performed by the FOC algorithm is always to align (and rotate) the combined magnetic field of the stator to be perpendicular to the rotor's magnetic field. This alignment causes the stator (magnetic) field to pull one side of the rotor and push the other side, rotating it with the maximum force. By design, the FOC algorithm sends energy into the stator coils to maximize the rotational force on the spinning rotor. Rotational force is called torque. The FOC algorithm produces maximum torque.

The operation of the field-oriented-control is accomplished by generating a very high-speed series of discrete control output voltages and simultaneously taking very high-speed measurements of discrete current samples. The waveforms are thus continuous signals generated by and measured through a series of discrete control settings and measured values. The FOC computation involves back-and-forth conversion of current and voltage waveforms and transformation to and from a "fixed" reference frame into and out of a "rotational" reference frame.

Proportional-Integral (PI) Closed-Loop control uses a feedback measurement of the PI-controller output and the desired output value, called the PI-controller reference, to move the PI-controller output to match the desired output value. The difference between the PI-controller output and the PI-controller reference is the PI-controller error. FOC uses closed-loop PI-controller(s) for several parts of its operation.

Referring to FIG. 10, the time scheduled PI control for $I_d$, $I_q$ and Speed 1030 includes the Speed PI controller 1032, which uses the estimated actual speed from the Position and Speed estimator 1026 and the reference speed from the Rate Limiter 1020 to output the $I_q$ quadrature current reference. Next, the $I_q$ PI controller 1034 uses this $I_q$ reference, the measured $I_q$ current, and the motor's physical parameters to output a v q quadrature voltage reference. Finally, the $I_d$ direct current PI controller 1034 uses an $I_d$ reference value of zero along with the measured $I_d$ current and the motor's physical parameters to output a $v_d$. (direct voltage) reference.

The $v_q$ and $v_d$ signals, which are voltage reference signals from the PI Controller 1030, are inputs to the FOC Transformations block 1040, specifically inputs to the Inverse Park transform 1042, which outputs $v_\alpha$ and $v_\beta$ rotational phase voltages, which become inputs to and is followed by operation of the Inverse Clarke transform 1044, which outputs $v_a$, $v_b$ and $v_c$, which are fixed reference frame phase voltages. These transformations thus perform the geometric conversion of voltage waveforms from the rotational frame $v_q/v_d$ to a fixed frame, $v_a$, $v_b$, $v_c$.

In FIG. 7, the Proportional Integral Controller1 (PI1) 750 outputs $v_q$, the quadrature voltage, to the Inverse Park Transform in logic 770. Also in FIG. 7, the Proportional Integral Controller2 (PI2) 752 outputs $v_d$. (the direct voltage) to the Inverse Park Transform in logic 770.

The Inverse Park Transform in logic 770 outputs $v_\alpha$ and $v_\beta$, the rotational phase vector voltages, to the Inverse Clarke Transform in logic 770, which outputs $v_a$, $v_b$, $v_c$, the three phase-voltage space vectors, directly to the SVPWM block 780. The Inverse Park and Inverse Clarke transformation logic 770 essentially performs the mathematics involved to convert a desired quadrature voltage (speed) and direct voltage into phase voltages needed to produce the voltage waveforms in the stator phases.

The Park and Clarke Transformation logic 720 first converts the $I_a$, $I_b$, $I_c$ phase current waveforms, stated in coordinates of the fixed reference frame and measured from the three stationary physically positioned wire coils in the stator, into two rotational phase currents, $I_\alpha$ and $I_\beta$, output from the Clarke Transform block 1046 in FIG. 10.

Then in the Park Transform block 1048, the rotational phase currents, $I_\alpha$ and $I_\beta$, are converted into the measured (or actual) values $I_q$ (actual quadrature current) and $I_d$ (actual direct current) waveforms seen in rotational frame coordinates. The $I_q$ (quadrature) and $I_d$ (direct) currents are the same currents represented in the "rotational" frame as the phase currents $I_a$, $I_b$, $I_c$, as represented in fixed reference frame.

As discussed, the Clarke Transform in logic 720 in FIGS. 7 and 1048 in FIG. 10 outputs the rotational phase currents $I_\alpha$ and $I_\beta$ and the Inverse Park transform in logic 770 in FIGS. 7 and 1042 in FIG. 10 outputs the rotational phase voltages $v_\alpha$ and $v_\beta$. The rotational phase voltages and rotational phase currents are all used by the Position and Speed Estimator 2026 to "close the loop", generating feedback values of the actual (estimated) speed that feeds back into the Speed Pi-controller 1032 and the rotor position angle output which is an input to both the Park 1048 and the Inverse Park 1042 transforms.

The Sensorless Field Oriented Control (SFOC) Algorithm is a processing loop that makes a single sample current measure from all of the motor stator phases, and then generates a single sample output value which changes the voltage waveform in those same phases. Then it loops back and operates again on another sample. The loop speed and the sample rate needs to be very fast when the rotor speed is into thousands and tens of thousands of RPM. Implementing the SFOC algorithm in FPGA, where the clock that times the loop operations is very fast and very stable, is the only way that this can be accomplished. A microprocessor might have the computational power to do the mathematical operations, but the processor clock and interrupt structures would not provide a stable, evenly timed operation for the loop control, especially at very high speeds. The dedicated FPGA logic would also actually do the mathematical operations faster than can be done with the microcontroller.

The system controller recognizes two different classes of events that can be detected. The first is alerts, which are deemed to be medium-priority events for which the user needs to be notified. The second is alarms, which are deemed to be high-priority events for which the user needs to be notified and for which the user needs to take immediate remedial action. Alerts are discussed with reference to FIGS. 11 and 12 below while alarms are discussed with reference to FIGS. 13 and 14.

Figure 11:
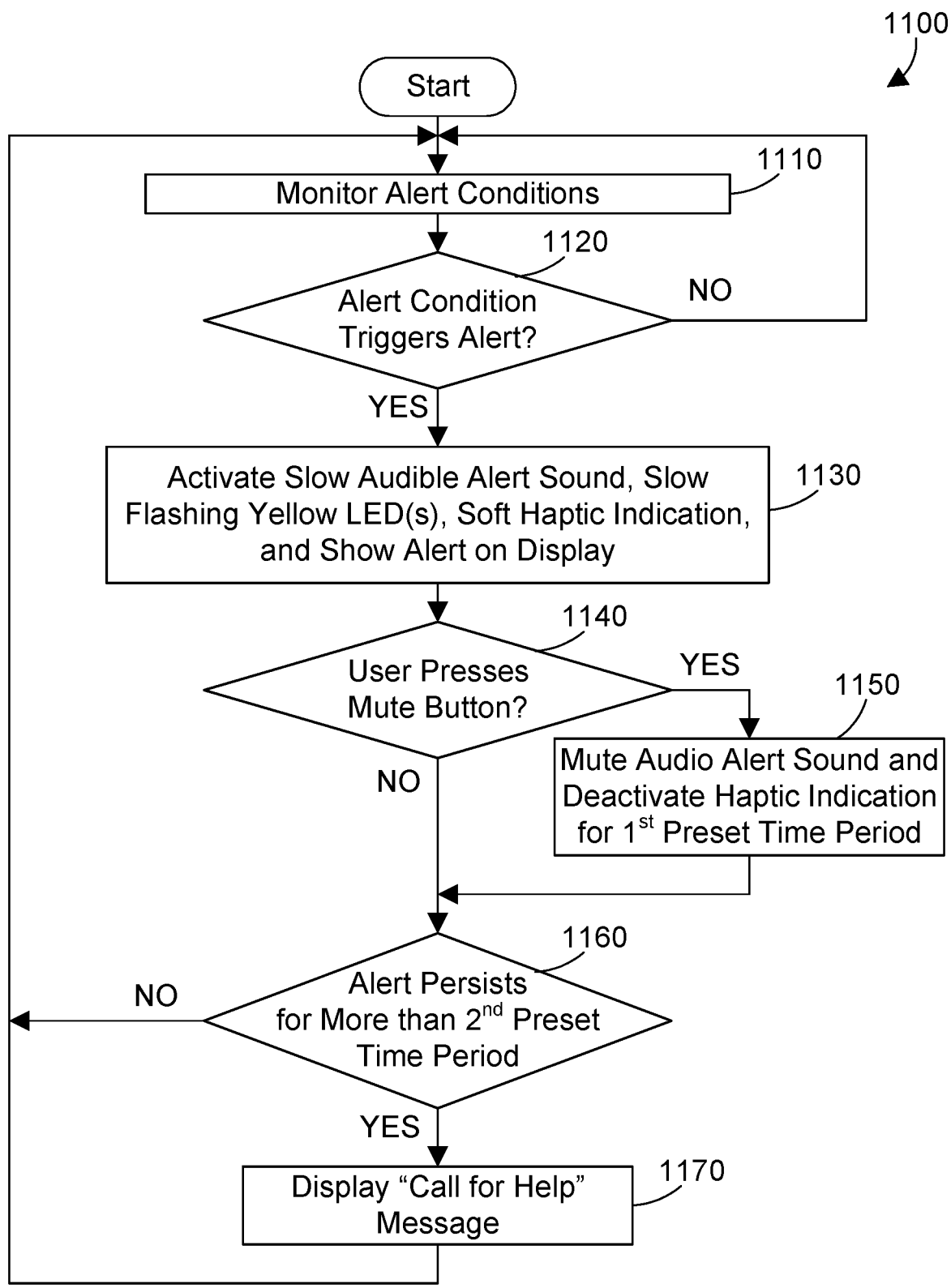
FIG. 11 is a flow diagram of a method for the system controller to monitor and process alerts.

Referring to FIG. 11, a method 1100 is preferably performed by the alert manager 474 in the control processor 470, as shown in FIG. 4. Monitor alert conditions (step 1110). As long as no alert condition triggers an alert (step 1120=NO), method 1100 loops back to step 1110 and continues. Once an alert condition triggers an alert (step 1120-YES), activate a slow audible alert sound, activate one or more slow flashing yellow LEDs, provide a soft haptic indication such as a mild vibration, and show the alert on the display (step 1130). If the user presses the mute button (step 1140=YES), which is one of the input keys 170, the audio alert sound is muted and the soft haptic indication is deactivated for a first preset time period, such as 15 seconds (step 1150). If the alert persists beyond a second preset time period, such as 20 seconds (step 1160=YES), a "Call for Help" message is displayed (step 1170). Method 1100 then loops back to step 1110 and continues.

As shown in FIG. 4, the control processor 470 includes an alert manager 474 and an alarm manager 476. Note the functions of these two could be combined. However, experience has shown a need for alerts, which are medium-priority events, to be handled differently than alarms, which are high-priority events. When all events are treated as high-priority alarms, this can lead to taking unnecessary and even life-threatening action when no such action is needed for medium-priority events. As a result, the controller disclosed and claimed herein differentiates between medium-priority events referred to as "alerts" herein and high-priority events referred to as "alarms" herein.

FIG. 12 shows a table 1200 that defines multiple alerts that can be detected and acted upon. Each row in table 1200 defines an alert according to a defined alert condition, the entity that detects the condition, and the notification message that is provided on the display as a result of the detected alert. In the Detected By column in FIG. 12, a CP is included for most of the alerts because most alerts can be detected by the control processor (CP). An SP is included for those alerts that can be detected by the supervisor processor (SP) independently from the CP. A pump low flow alert 1210 is detected by the CP, and a Pump Low Flow message is displayed. A Pump Power Over Current alert 1212 is detected by the CP, and a Pump Power High message is displayed. A Pump Power High alert 1214 is detected by the CP, and a Pump Power High message is displayed. A Pump Power Low alert 1216 is detected by the CP, and a Pump Power Low message is displayed. A Pump Speed Low alert 1218 is detected by the CP, and a Pump Speed Low message is displayed. A Pump Speed Error alert 1220 is detected by the CP, and a Pump Speed Error message is displayed. A System Over Temp alert 1222 is detected by the CP, and a System Fault message is displayed. A Reserve Battery Fault alert 1224 is detected by the CP, and a System Fault message is displayed. A Reserve Battery Low alert 1226 is detected by the CP, and a Reserve Low message is displayed. A Reserve Battery Discharging alert 1228 is detected by the CP, and an On Reserve message is displayed. A Primary Battery Low alert 1230 is detected by the CP, and a Battery Low message is displayed. A Primary Battery Very Low alert 1232 is detected by the CP, and a Battery Very Low message is displayed. A Primary Battery Critical alert 1234 is detected by the CP, and Battery Critical message is displayed. A Control Processor or FPGA Bad alert 1236 is detected by the SP, and a System Fault message is displayed. A DC Input Bad alert 1238 is detected by the CP, and a System Fault message is displayed. A Software Failure alert 1240 is detected by the SP, and a System Fault message is displayed. A Mute Button Stuck alert 1242 is detected by the CP, and a System Fault message is displayed. A Next Button Stuck alert 1246 is detected by the CP, and a System Fault message is displayed. An Alert Test alert 1248 is detected by the CP, and an Alert Test message is displayed. The alerts shown in FIG. 12, along with any other suitable alerts, are within the scope of the disclosure and claims herein.

The alerts are, by definition, less severe than alarms. As a result, the patient should only see/hear/feel a medium priority notification for alert conditions that the Clinician needs to know about more immediately. For all of these alerts, the Patient may also be instructed to call the Clinic for help. The instruction to "CALL FOR HELP" can be indicated, for example, with an illuminated phone icon on the front face of the controller and a "CALL FOR HELP" message on the controller display. An alert message has an alert number in it that the patient can read to the clinical personnel when the patient calls for help. Even those alerts that do not require notifying a clinician are logged.

The specific alerts shown in FIG. 12 are shown by way of example. Other alert conditions could be detected resulting in corresponding notifications within the scope of the disclosure and claims herein. In addition, while most of the alerts in FIG. 12 are shown to be detected by the CP alone, in an alternative implementation the Service Processor (SP) could also monitor many of the alert conditions detected by the CP, and could provide alert notifications independently from the CP. This is very beneficial in the case of failure of the CP.

Figure 13:
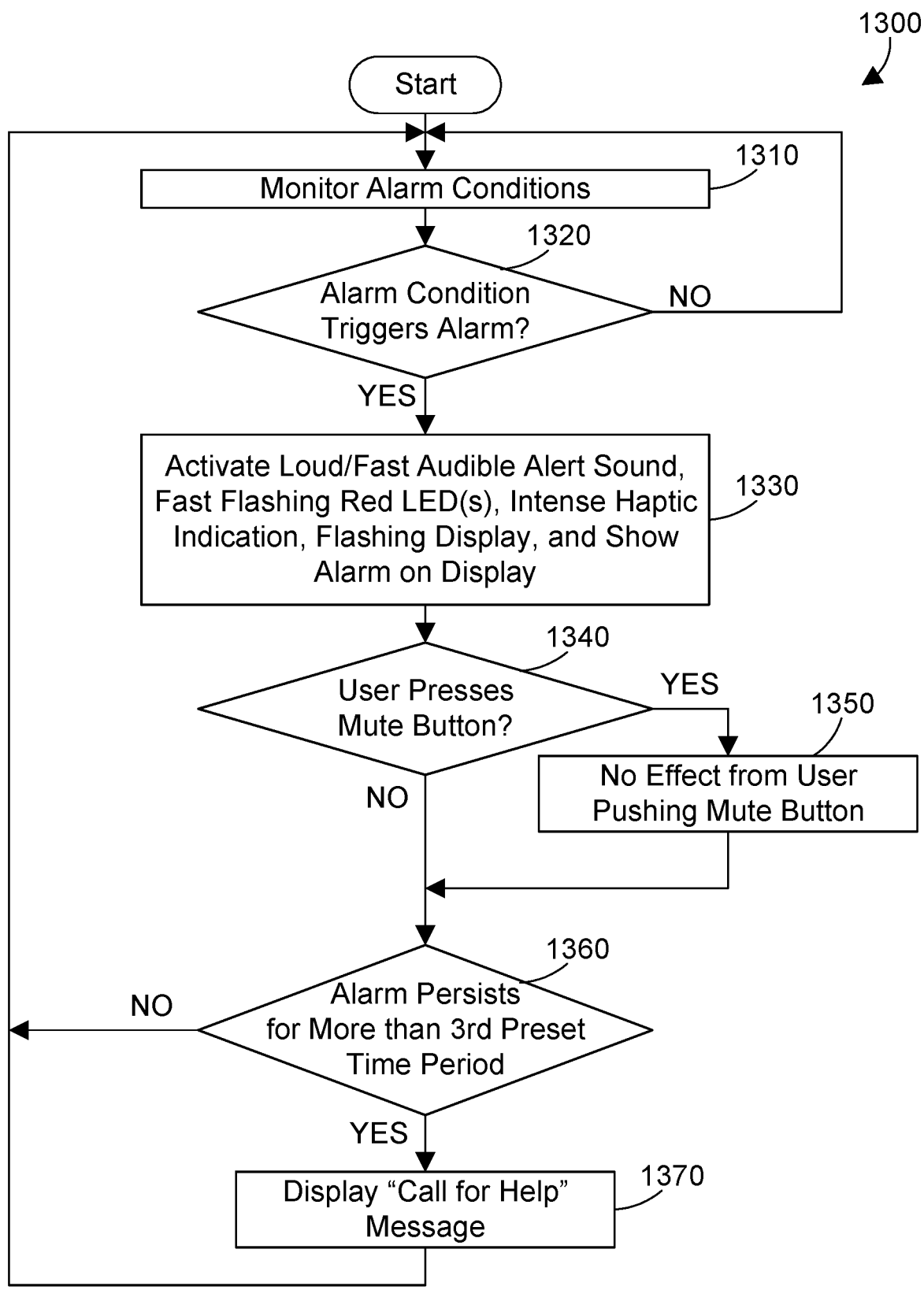
FIG. 13 is a flow diagram of a method for the system controller to monitor and process alarms.

Referring to FIG. 13, a method 1300 is preferably performed by the alarm manager 476 in the control processor 470, as shown in FIG. 4. Monitor alarm conditions (step 1310). As long as no alarm condition triggers an alarm (step 1320=NO), method 1300 loops back to step 1310 and continues. Once an alarm condition triggers an alarm (step 1320=YES), activate a loud and fast audible alert sound, activate one or more fast flashing red LEDs, provide an intense haptic indication such as a hard vibration, and show the alarm on the display (step 1330). If the user presses the mute button (step 1340=YES), this has no effect (step 1350) because, while alerts can be muted by the user for a predefined time period, alarms cannot. If the alarm persists beyond a third preset time period, such as 20 seconds (step 1360=YES), a "Call for Help" message is displayed (step 1370). Method 1300 then loops back to step 1310 and continues.

Figures 14, 15:
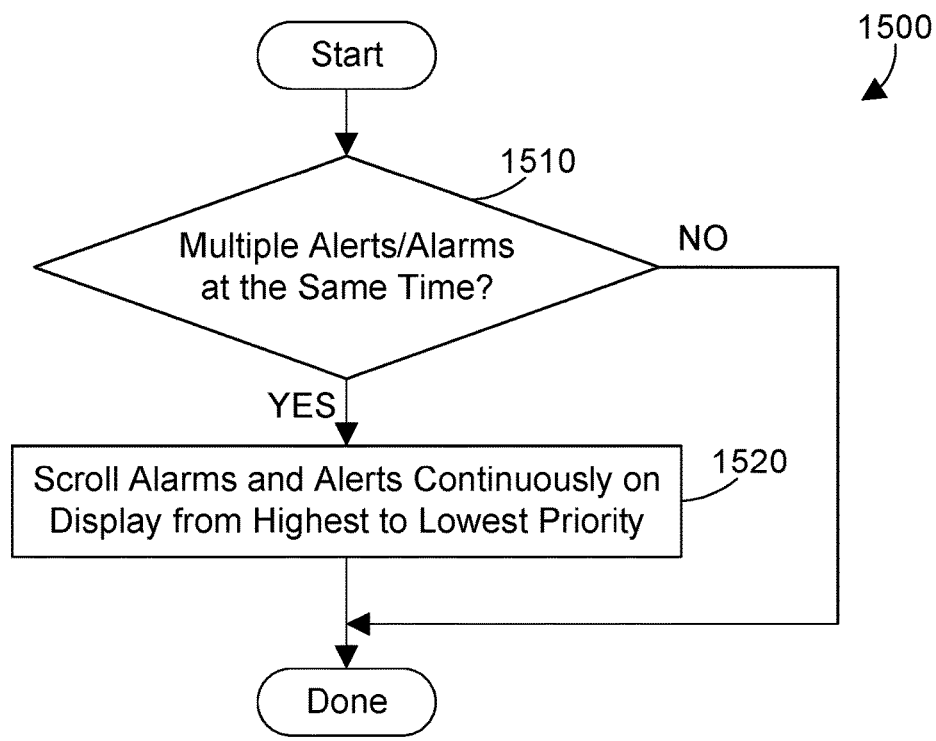
FIG. 14 is a table showing alarm conditions and corresponding notifications.
FIG. 15 is a flow diagram of a method for displaying on the system controller display multiple alarms and/or alerts that are active at the same.

FIG. 14 shows a table 1400 that defines multiple alarms that can be detected and acted upon. Each row in table 1400 defines an alarm according to a defined alarm condition, the entity or entities that can detect the condition, and the notification that is written to the display as a result of the detected alarm. A Pump Stopped alarm 1410 is detected by the CP and SP, and a Pump Stopped notification is displayed. The pump can stop for a variety of reasons, including: the pump driveline is cut, broken, unplugged, or otherwise broken; the FPGA motor control can no longer spin the pump motor; the controller loses power; the only power supply is a depleted internal reserve battery that can no longer supply enough current to run the pump; the pump occludes with thrombus; or the pump motor itself is malfunctioning or otherwise broken. A Pump Disconnect alarm 1412 is detected by the CP, and a Pump Disconnect message is displayed. A Pump Re-Start Fail alarm 1414 is detected by the CP, and a Pump Re-Start Fail message is displayed. A No Primary Battery alarm 1416 is detected by the CP, and a No Battery message is displayed. An Emergency Alarm Test alarm 1418 is detected by the CP, and an Alarm Test message is displayed. An Alarm Test alarm 1420 is detected by the CP, and an Alarm Test message is displayed. A Power Supply Fail alarm 1422 is detected by the SP, and an Emergency Alarm message is displayed. In one suitable implementation, the SP monitors the regulated power supplies in the control system, and if any of the regulated power supplies are not providing voltages within specified ranges, the SP can detect this condition and provide the Emergency Alarm in response to detecting this power supply failure. The alarms shown in FIG. 14, along with any other suitable alarms, are within the scope of the disclosure and claims herein. Furthermore, many of the alarms in FIG. 14 that are detected by the CP could additionally be detected by the SP in alternative embodiments.

The alarm and alert messages output to the display have a straightforward format; an alarm or alert label, with a numeric identifier, followed by a simple instruction for how to rectify the condition (if possible), and potentially one or two additional instructions, such as "CALL FOR HELP" or "CALL FOR HELP" and "REPLACE CONTROLLER."

There may be times when there are multiple alerts and/or alarms at the same time. The control processor 470 preferably performs method 1500 in FIG. 15. When there are not multiple alerts and/or alarms at the same time (step 1510=NO), method 1500 is done. When there are multiple alerts and/or alarms at the same time (step 1510=YES), scroll the alarms and alerts continuously on the display from the highest to lowest priority (step 1520). By scrolling multiple alerts/alarms on the display, a user can easily see all pending alerts and alarms as the messages scroll on the display. Method 1500 is then done.

While the alert manager 474 and alarm manager 476 are shown in FIG. 4 to be separate entities, the functions of both could be provided by software in the control processor.

Figure 16:
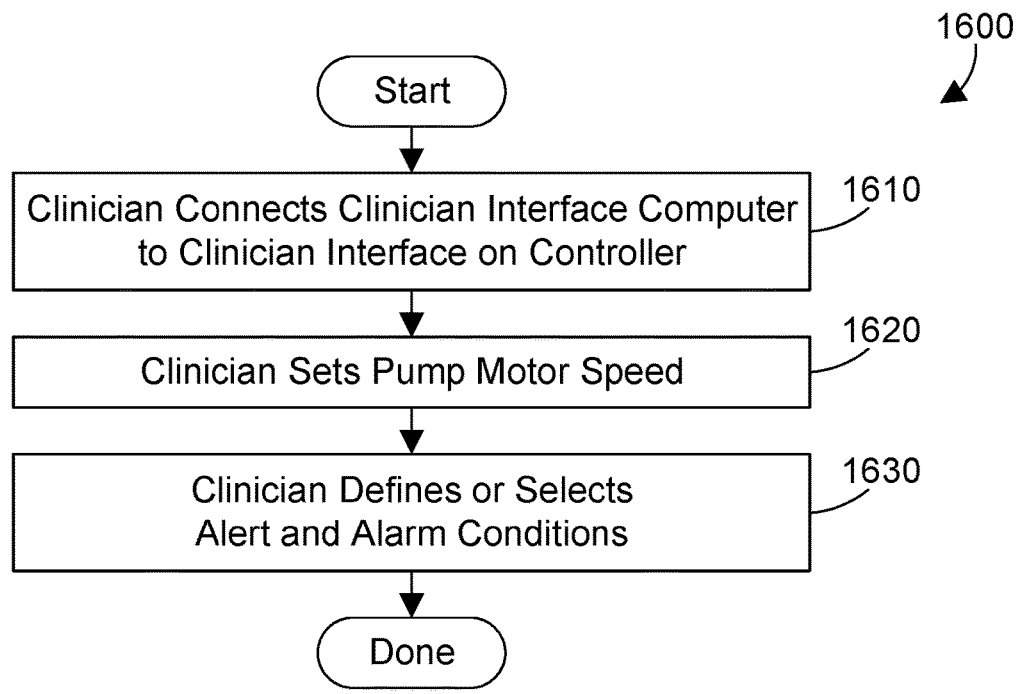
FIG. 16 is a flow diagram of a method for a clinician to program the system controller for a particular patient.

FIG. 16 shows a method 1600 for a clinician to program the blood pump. The clinician connects a clinician interface computer to the clinician interface on the controller (step 1610). The clinician interface computer can be any suitable computing device, including without limitation a desktop computer, a laptop computer, a tablet computer, or a smart phone. The clinician invokes the GUI in the clinician interface, and uses the GUI to set the pump motor speed (step 1620). The clinician can also define or select alert and alarm conditions (step 1630), such as thresholds for one or more alert or alarm conditions. Method 1600 is then done.

Figure 17:
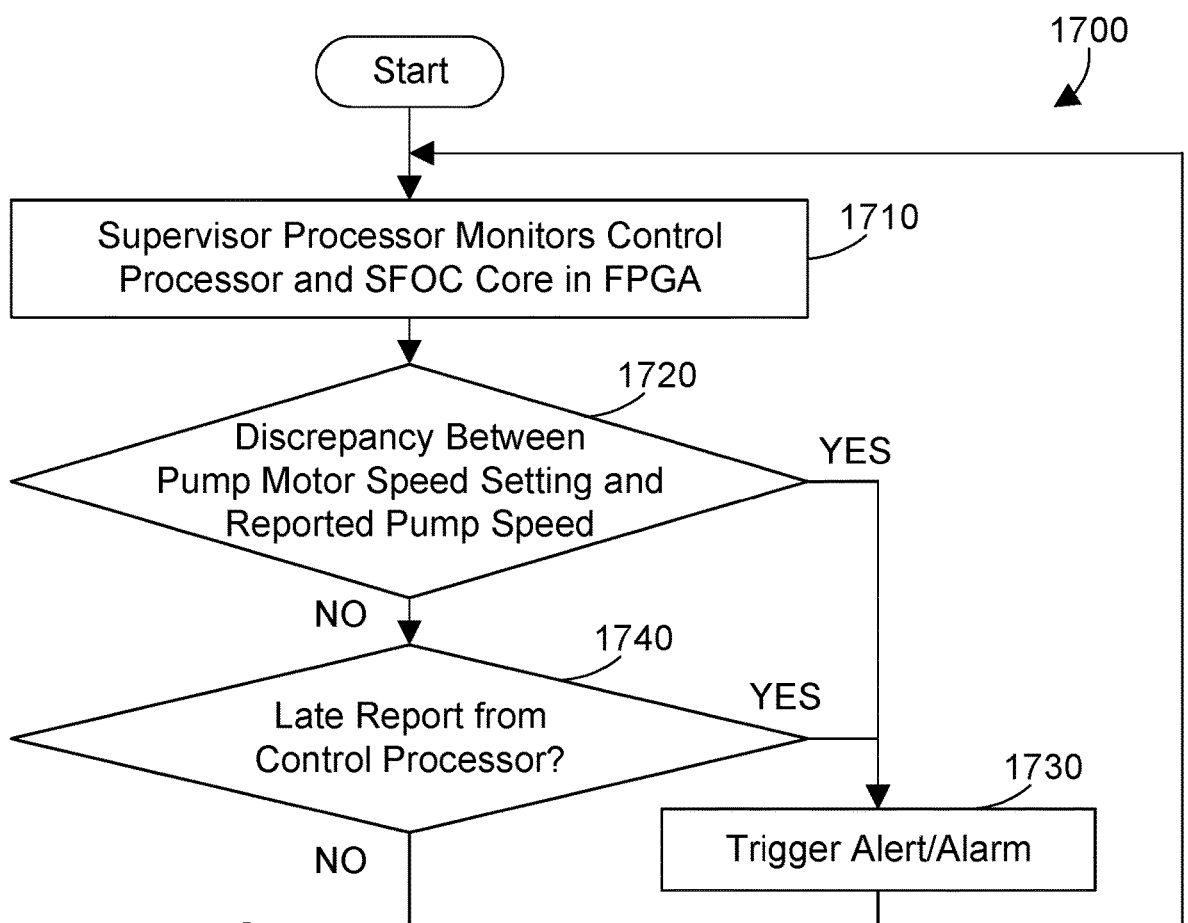
FIG. 17 is a flow diagram of a method for the supervisor processor to trigger an alarm when an error occurs in the FPGA motor controller or the system controller.

As discussed above with reference to FIG. 3, the presence of a supervisor processor 320 allows monitoring the health and well-being of the control processor 330 and the FPGA motor control 340. Method 1700 in FIG. 17 is preferably performed by the supervisor processor 320 shown in FIG. 3. The supervisor processor monitors the control processor and the SFOC Core in the FPGA (step 1710). When there is a discrepancy between the pump motor speed setting and the reported pump speed (step 1720=YES), an alert or alarm is triggered (step 1730). When there is no discrepancy in step 1720 (step 1720=NO) but there is a late report from the control processor (step 1740=YES), an alert or alarm is triggered (step 1730). Method 1700 then loops back to step 1710 and continues. We see from method 1700 that the supervisor processor has the ability to detect issues with both the control processor and SFOC Core in the FPGA, thereby providing another layer of protection should one or both of the control process and/or SFOC core quit working properly. In some cases, if the system controller is really not functioning correctly, the triggered alarm would be to replace the system controller immediately.

Figure 18:
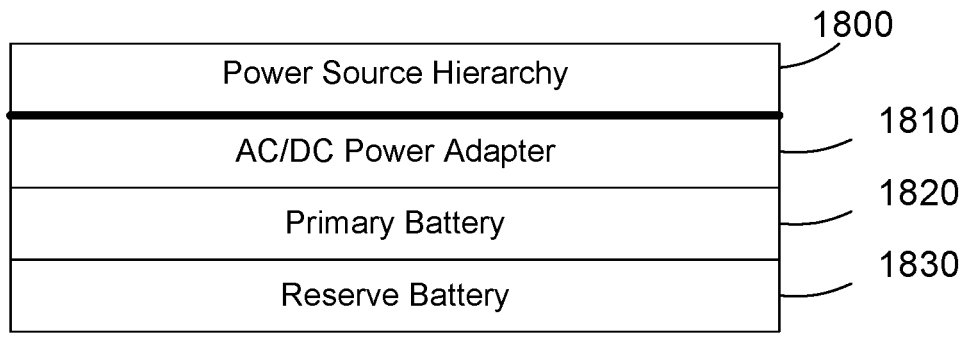
FIG. 18 is a block diagram of a hierarchy used by a power controller within the system controller to determine which power source will power the system controller.

As discussed above with reference to FIG. 2, the system controller 210 functions according to a defined power source hierarchy. The system controller 470 in FIG. 4 shows a power manager 478 that manages power from three sources, namely a primary battery, an AC/DC power adapter, and a reserve battery. One suitable power source hierarchy that could be used by the power manager 478 in FIG. 4 is shown in table 1800 in FIG. 18, where the hierarchy is defined from highest priority to lowest priority. Thus, AC/DC power adapter 1810 is the highest priority, meaning when power is present from the AC/DC power adapter, the power manager 478 will use power from the AC/DC power adapter. The primary battery 1820 is next in priority, which means when no power is present from the AC/DC power adapter, which could be caused by the AC/DC power adapter being unplugged from the system controller or due to a power outage, the power manager 478 will use power from the primary battery. The reserve battery 1830 inside the housing of the system controller is the lowest priority. Thus, the power manager 478 will only use power from the reserve battery when there is no power available from either the AC/DC power adapter or the primary battery. The reserve battery is designed only to be used for very short periods of time between switching primary batteries, so the reserve battery does not have sufficient capacity to run the system controller and blood pump for any extended period of time. The reserve battery is designed to run the blood pump for 30 minutes under nominal conditions, which means the reserve battery will be more than enough for the typical minute or two it takes a user to switch primary battery packs.

Figure 19:
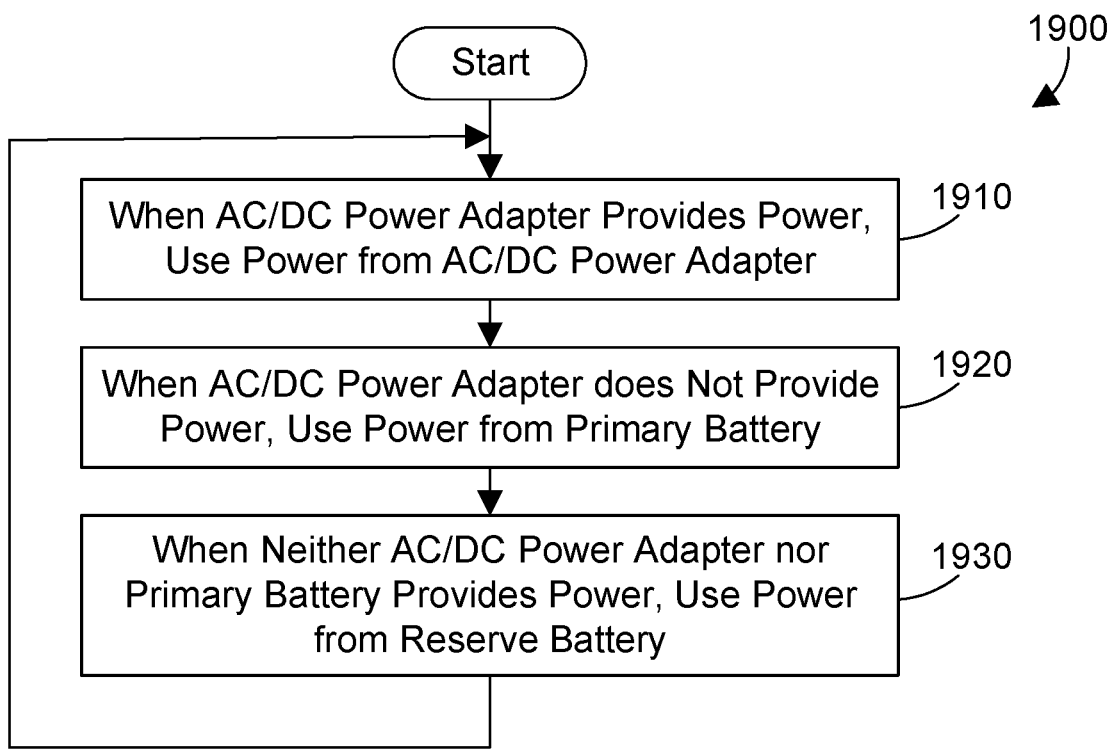
FIG. 19 is a flow diagram of a method for the system controller to determine which power source to use according to the power source hierarchy in FIG. 18.

Method 1900 in FIG. 19 is preferably performed by the power manager 478 in FIG. 4. When the AC/DC power adapter provides power, use the power from the AC/DC power adapter (step 1910). When the AC power adapter does not provide power, use power from the primary battery (step 1920). When neither the AC/DC power adapter nor the primary battery provides power, use power from the reserve battery (step 1930). Method 1900 then loops back to step 1910 and continues.

While the power manager 478 is shown in FIG. 4 to be a function provided by the control processor 470, in a preferred embodiment the functions of the power manager 478 are performed by a separate power management integrated circuit that communicates power status to the control processor.

Figure 20:
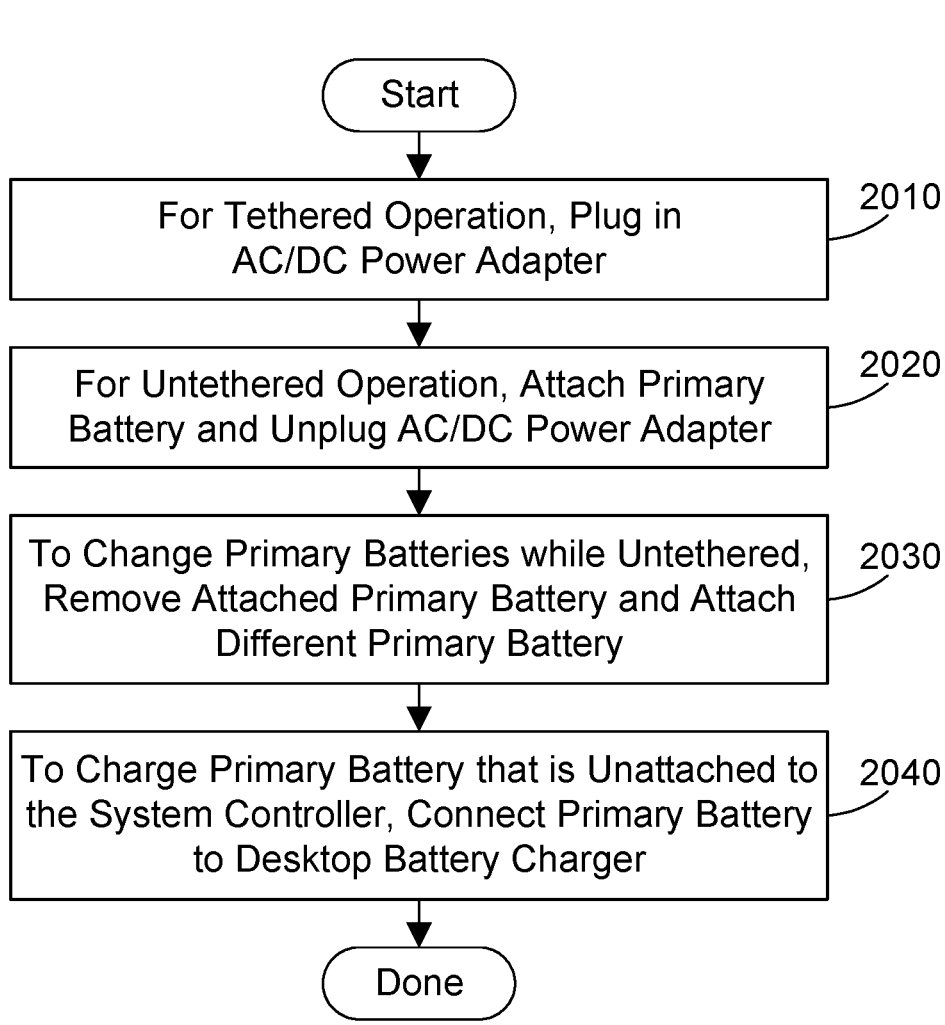
FIG. 20 is a flow diagram of a method showing various uses of the system controller by a patient.

FIG. 20 is a method 2000 that shows different modes of operation for the system controller and blood pump. For tethered operation, where the user is going to be in one place near an electrical outlet for a while, the user can plug in the AC/DC power adapter (step 2010). For untethered operation, where the use is not in one place near an electrical outlet, attach a primary battery and then unplug the AC/DC power adapter (step 2020). Because the system controller can be used for untethered operation, the system controller is a wearable device where the size, weight and temperature are considerations in the wearability of the system controller. To change primary batteries while untethered, remove the attached primary battery and replace it by attaching a different primary battery (step 2030). To charge a primary battery that is unattached to the system controller, connect the primary battery to the desktop battery charger (step 2040). In a preferred embodiment, the mechanical and electrical connections between the primary battery and the desktop battery charger are identical to the mechanical and electrical connections between the primary battery and the system controller. This allows a user to use the same motions to disconnect and connect a primary battery to/from the desktop battery charger that the user uses to disconnect and connect a primary battery to/from the system controller.

Figure 21:
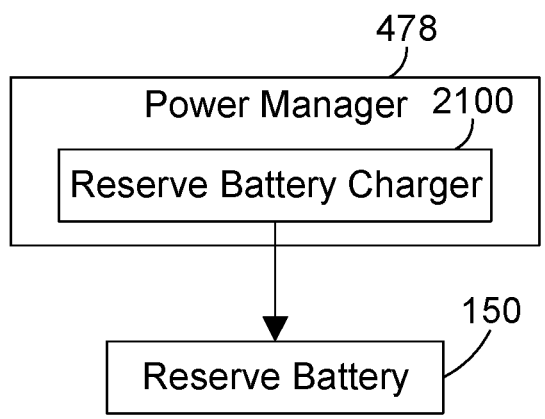
FIG. 21 is a block diagram showing a reserve power charger in the power manager that charges the internal reserve battery when certain conditions are met.
Figure 22:
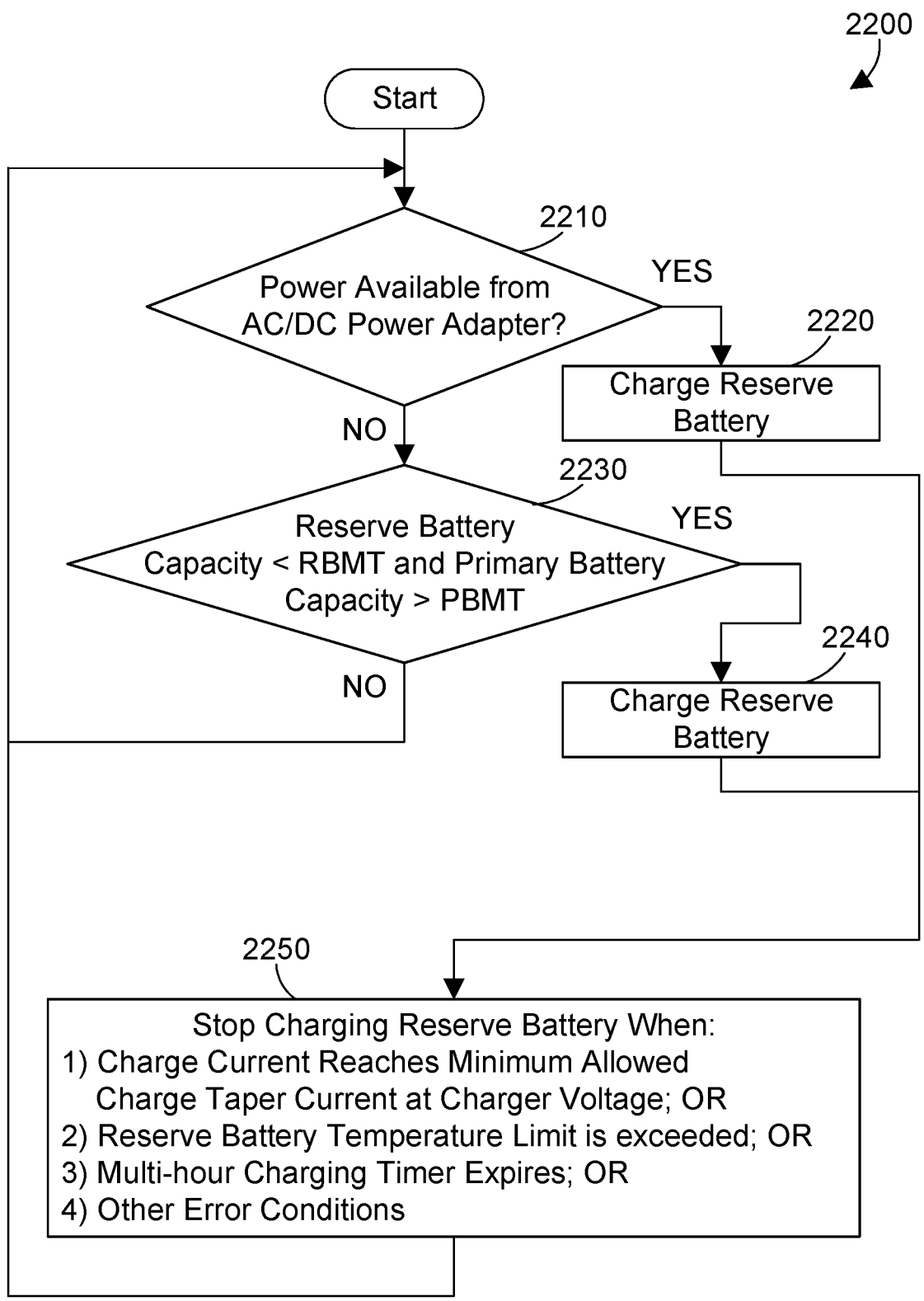
FIG. 22 is a flow diagram of a method for the reserve battery charger in FIG. 21 to charge the reserve battery.

As shown in FIG. 21, the power manager 478 shown in FIG. 4 preferably includes a reserve battery charger 2100 for charging the reserve battery 150. The reserve battery charger 2100 preferably functions according to method 2200 in FIG. 22. When power is available from the AC/DC power adapter (step 2210=YES), charge the reserve battery (step 2220). When power is not available from the AC/DC power adapter (step 2210=NO), but the reserve battery capacity is less than a reserve battery minimum threshold RBMT and the primary battery capacity is above a primary battery minimum threshold PBMT (step 2230=YES), charge the reserve battery (step 2240). Otherwise (step 2230=NO), the reserve battery is not charged, and method 2200 loops back to step 2210. Once the reserve battery is being charged in steps 2220 or 2240, charging can stop when any of the following conditions listed in step 2250 are satisfied, namely: 1) the charge current for the reserve battery reaches a minimum allowed charge taper current at the charger voltage; or 2) the reserve battery temperature limit is exceeded; or 3) a multi-hour charging timer expires; or 4) other error conditions. The reserve battery charger thus attempts to keep the reserve battery fully charged to it has the capacity to satisfy short interruptions in power from the AC/DC power adapter and the primary battery.

A blood pump system includes a blood pump and a corresponding controller. The blood pump includes an impeller that is sealed within the pump housing and hydrodynamically suspended within the pump housing. The pump impeller includes magnets, and is the rotor of a brushless direct current (DC) motor that is driven by electrical signals through stator wire coils in the pump housing, which creates a rotating magnetic field. The rotating magnetic field attracts the magnetized impeller and spins it with the rotating field. The controller provides field-oriented control for the brushless DC motor in the blood pump. The field-oriented control in the controller is provided in a programmable logic device separate from a control processor so that a software or hardware failure related to the control processor does not stop the blood pump. The field-oriented control allows sensing blood flow through the pump without having sensors in the blood stream.

The disclosure and claims herein support a system controller for driving a blood pump comprising an impeller sealed within a pump housing and hydrodynamically suspended in the pump housing, wherein the impeller comprises a plurality of magnets, the blood pump comprising a plurality of stator coils in a brushless direct current (DC) motor that, when driven by a plurality of drive signals, make the impeller rotate within the pump housing, wherein the system controller comprises: an electrical connector for electrically connecting the system controller to the blood pump to provide the plurality of drive signals from the system controller to the plurality of stator coils in the brushless DC motor in the blood pump; a display; a control processor that provides management functions for the system controller and that displays at least one message on the display; and a programmable logic device that provides field-oriented control of the brushless DC motor in the blood pump by providing the plurality of drive signals to the plurality of stator coils in the brushless DC motor in the blood pump via the electrical connector, wherein the programmable logic device functions independently of the function or not of the control processor.

The disclosure and claims herein further support a system controller for driving a blood pump comprising an impeller sealed within a pump housing and hydrodynamically suspended in the pump housing, wherein the impeller comprises a plurality of magnets, the blood pump comprising a plurality of stator coils in a brushless DC motor that, when driven by a plurality of drive signals, make the impeller rotate within the pump housing, wherein the system controller comprises: an electrical connector for electrically connecting the system controller to the blood pump to provide the plurality of drive signals from the system controller to the plurality of stator coils in the brushless DC motor in the blood pump; a display; at least one input key for a user of the system controller; at least one visual indicator for the user; at least one audio device for signaling to the user an alert or alarm condition; a reserve battery internal to a housing for the system controller that provides power when an external primary battery does not provide power to the system controller and when an external AC/DC adapter does not provide power to the system controller; a clinician interface that provides a graphical user interface that allows a medical clinician to set speed of the blood pump and to define or select at least one alert or alarm condition in the system controller using a clinician computer coupled to the clinician interface; a control processor that provides management functions for the system controller, that displays at least one message on the display, and that activates at least one of the visual indicator and the at least one audio device to signal an alert or alarm condition; and a programmable logic device that provides field-oriented control of the brushless DC motor in the blood pump by providing the plurality of drive signals to the plurality of stator coils in the brushless DC motor in the blood pump via the electrical connector, wherein the programmable logic device functions independently of the function or not of the control processor.

The disclosure and claims herein additionally support a blood pump system comprising: (A) a blood pump comprising: an impeller sealed within a pump housing and hydrodynamically suspended in the pump housing, wherein the impeller comprises a plurality of magnets; a plurality of stator coils in a brushless DC motor that, when driven by a plurality of drive signals, make the impeller rotate within the pump housing; (B) a system controller electrically coupled to the blood pump that provides the plurality of drive signals to the plurality of stator coils in the brushless DC motor in the blood pump, the system controller comprising: a display; a control processor that provides management functions for the system controller and that displays at least one message on the display; and a programmable logic device that provides field-oriented control of the brushless DC motor in the blood pump by providing the plurality of drive signals to the plurality of stator coils in the brushless DC motor in the blood pump independently of the function or not of the control processor.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

The invention claimed is:

1. A system controller for driving a blood pump comprising an impeller sealed within a pump housing and hydrodynamically suspended in the pump housing, wherein the impeller comprises a plurality of magnets, the blood pump comprising a plurality of stator coils in a brushless direct current (DC) motor that, when driven by a plurality of drive signals, make the impeller rotate within the pump housing, wherein the system controller comprises:
    an electrical connector for electrically connecting the system controller to the blood pump to provide the plurality of drive signals from the system controller to the plurality of stator coils in the brushless DC motor in the blood pump;
    a display;
    a control processor that provides management functions for the system controller and that displays at least one message on the display; and
    a programmable logic device that provides field-oriented control of the brushless DC motor in the blood pump by providing the plurality of drive signals to the plurality of stator coils in the brushless DC motor in the blood pump via the electrical connector, wherein the programmable logic device is configured to continue providing the plurality of drive signals when the control processor stops working.

2. The system controller of claim 1 further comprising a reserve battery internal to the system controller.

3. The system controller of claim 2 further comprising a power manager that selects a power source for powering the system controller according to a defined power source hierarchy, wherein the power source is selected from: power from an AC/DC adapter coupled to a first exterior connector on the system controller; power from a primary battery coupled to a second exterior connector on the system controller; and power from the reserve battery internal to the system controller.

4. The system controller of claim 1 wherein the programmable logic device comprises a Field-Programmable Gate Array (FPGA).

5. The system controller of claim 1 wherein the control processor and the programmable logic device are implemented in a system-on-a-chip (SoC).

6. The system controller of claim 1 further comprising:
    at least one input key for a user of the system controller;
    at least one visual indicator for the user; and
    at least one audio device for signaling to the user an alert or alarm condition.

7. The system controller of claim 1 further comprising a clinician interface that provides a graphical user interface that allows a medical clinician to set speed of the blood pump and to define or select at least one alert or alarm condition in the system controller using a clinician computer coupled to the clinician interface.

8. The system controller of claim 1 further comprising a supervisor processor coupled to the control processor and the programmable logic device, wherein the supervisor processor monitors function of the control processor and the programmable logic device according to at least one monitored parameter and provides an alert or alarm signal when the at least one monitored parameter indicates an alert or alarm condition.

9. The system controller of claim 1 further comprising an alert manager that allows defining or selecting a plurality of alerts and corresponding alert notifications, that detects when one of the plurality of alerts is triggered, and provides at least one notification corresponding to the triggered one alert.

10. The system controller of claim 1 further comprising an alarm manager that allows defining or selecting a plurality of alarms and corresponding alarm notifications, that detects when one of the plurality of alarms is triggered, and provides at least one notification corresponding to the triggered one alarm.

11. The system controller of claim 1 further comprising a motor driver integrated circuit that receives pulse-width modulated drive signals from the programmable logic device and generates the plurality of drive signals to the plurality of stator coils in the brushless DC motor in the blood pump.

12. The system controller of claim 1 further comprising a digital motor current conversion circuit that receives current sensed in each of the plurality of drive signals to the blood pump and generates therefrom digital motor current values that are fed back into the programmable logic device.

13. The system controller of claim 12 wherein the field-oriented control performs Park and Clarke transformations on the digital motor current values to determine a magnetizing (direct) motor current and a torque-producing (quadrature) motor current, uses a first proportional integral controller to compare the magnetizing (direct) motor current with a reference direct current to generate a direct voltage signal, uses a second proportional integral controller to compare the torque-producing (quadrature) motor current with a reference quadrature current proportional to a desired motor speed signal to generate a quadrature voltage signal, performs an inverse Park transformation on the direct and quadrature voltage signals to generate two rotational phase voltage signals and then performs an Inverse Clarke transformation on the two rotational voltage signals to generate a pulse-width modulated duty cycle signal in phase space, uses a space vector modulation control block to generate a plurality of pulse width modulated signals that are used to drive the plurality of stator coils.

14. A system controller for driving a blood pump comprising an impeller sealed within a pump housing and hydrodynamically suspended in the pump housing, wherein the impeller comprises a plurality of magnets, the blood pump comprising a plurality of stator coils in a brushless DC motor that, when driven by a plurality of drive signals, make the impeller rotate within the pump housing, wherein the system controller comprises:

an electrical connector for electrically connecting the system controller to the blood pump to provide the plurality of drive signals from the system controller to the plurality of stator coils in the brushless DC motor in the blood pump;

a display;

at least one input key for a user of the system controller;

at least one visual indicator for the user;

at least one audio device for signaling to the user an alert or alarm condition;

a reserve battery internal to a housing for the system controller that provides power when an external primary battery does not provide power to the system controller and when an external AC/DC adapter does not provide power to the system controller;

a clinician interface that provides a graphical user interface that allows a medical clinician to set speed of the blood pump and to define or select at least one alert or alarm condition in the system controller using a clinician computer coupled to the clinician interface;

a control processor that provides management functions for the system controller, that displays at least one message on the display, and that activates at least one of the visual indicator and the at least one audio device to signal an alert or alarm condition; and a programmable logic device that provides field-oriented control of the brushless DC motor in the blood pump by providing the plurality of drive signals to the plurality of stator coils in the brushless DC motor in the blood pump via the electrical connector, wherein the programmable logic device is configured to continue providing the plurality of drive signals when the control processor stops working.

\* \* \* \* \*